(12) United States Patent
Takagi et al.

(10) Patent No.: US 6,762,200 B2
(45) Date of Patent: Jul. 13, 2004

(54) OXA(THIA)ZOLIDINE DERIVATIVE AND ANTI-INFLAMMATORY DRUG

(75) Inventors: Masae Takagi, Kanagawa (JP); Keiichi Ishimitsu, Kanagawa (JP); Tadayuki Nishibe, Kanagawa (JP)

(73) Assignee: Nippon Soda Co. Ltd., Tokyo (JP)

( * ) Notice: Subject to any disclaimer, the term of this patent is extended or adjusted under 35 U.S.C. 154(b) by 0 days.

(21) Appl. No.: 10/240,075

(22) PCT Filed: Mar. 27, 2001

(86) PCT No.: PCT/JP01/02481

§ 371 (c)(1),
(2), (4) Date: Sep. 25, 2002

(87) PCT Pub. No.: WO01/72723

PCT Pub. Date: Oct. 4, 2001

(65) Prior Publication Data

US 2003/0199479 A1 Oct. 23, 2003

(30) Foreign Application Priority Data

Mar. 28, 2000 (JP) ........................................ 2000-088078
May 15, 2000 (JP) ........................................ 2000-141395
Jun. 19, 2000 (JP) ........................................ 2000-182811

(51) Int. Cl.[7] ...................... A61K 31/44; C07D 263/04; A61P 29/00
(52) U.S. Cl. ...................... 514/377; 548/233; 546/135; 514/306
(58) Field of Search ........................ 548/233; 546/135; 514/377, 306

(56) References Cited

U.S. PATENT DOCUMENTS

| | | | |
|---|---|---|---|
| 4,446,209 A | 5/1984 | Iwakura et al. | |
| 4,568,766 A | 2/1986 | Yahagi et al. | |
| 4,866,083 A | * 9/1989 | Schoenwald et al. | 514/374 |
| 5,284,978 A | 2/1994 | Kinishi et al. | |

FOREIGN PATENT DOCUMENTS

| | | |
|---|---|---|
| EP | 0 081 584 A1 | 6/1983 |
| JP | 58-20493 | 5/1983 |
| JP | 60-56949 A | 2/1985 |
| JP | 63041471 * | 2/1988 |
| JP | 3-258760 A | 11/1991 |
| JP | 5-255234 | 5/1993 |
| JP | 6-25148 | 1/1994 |
| JP | 10-158235 | 6/1998 |

OTHER PUBLICATIONS

Ishimitsu et al., 1988, "Preparation of oxazolidine and thiazolidines . . . ", CAS:109:630998.*
JP Pat. Application KOKAI publication No. 63–41470.
JP Pat. Application KOKAI publication No. 63–41471.
Tetrahedron Lett., 32(42), pp. 5987 to 5990, (1991).
Irvine, R., Biochemical Journal 204: 3–16 (1982).
Glaser, K.B., Advances in Pharmacology 32: 31–66 (1995).
Dennis, E. A., Trends in Biochemical Science, 22: 1–2 (1997).
Balsinde, J. et al, Annual Review of Pharmacology and Toxicology, 39: 175–189 (1999).
Uozumi, N. et al, Nature 390: 619–622 (1997).
Bonventre, J.V. et al, Nature 390: 622–625 (1997).

* cited by examiner

*Primary Examiner*—Rita Desai
*Assistant Examiner*—Robert Shiao
(74) *Attorney, Agent, or Firm*—Dennis G. LaPointe; Mason Law, P.L.

(57) ABSTRACT

The present invention provides medicinal compositions characterized by containing as the active ingredient either a compound represented by a general formula (1) or a pharmaceutically acceptable composite thereof,

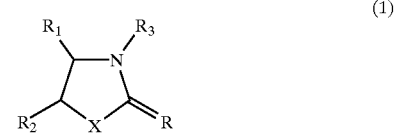

(1)

[wherein X represents oxygen or sulfur; $R_1$ represents hydrogen, $C_{1-4}$ alkyl, etc.; $R_2$ represents, e.g., phenyl optionally substituted by $A_1$; $R_3$ represents, e.g., hydrogen, $C_{1-4}$ alkyl optionally substituted by $A_2$, or a group represented by either one of the following formulae;

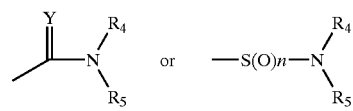

R represents oxygen, sulfur, or a group represented by a formula (N—G)], in particular, inhibitors of phospholipase A(2) activity; use of the compositions; and compounds represented by a general formula (1—1);

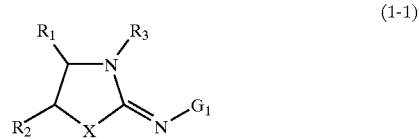

(1-1)

wherein X, $R_1$, $R_2$, $R_3$ and $G_1$ are the same as defined in the description.

8 Claims, No Drawings

OXA(THIA)ZOLIDINE DERIVATIVE AND ANTI-INFLAMMATORY DRUG

FIELD OF THE INVENTION

The present invention relates to inhibitor compositions of phospholipase A(2) (hereinafter referred to as PLA (2)) activity characterized by comprising as the active ingredient either an oxa(thia)zolidine derivative or a pharmaceutically acceptable composite thereof, a use of said inhibitor compositions in mammalian which require to relieve sick conditions accompanied by the enhanced PLA(2) activity, and novel oxa(thia)zolidine derivatives which are useful as an active ingredient for said inhibitor compositions.

BACKGROUND OF THE INVENTION

Inflammation is a series of defensive response process caused in the tissues, induced by the applied injurious events (inflammatory stimuli) on any parts of a human body. When the tissues are damaged by inflammatory stimuli that could be caused by bacterial infections, immunological responses or physical injuries, the tissues respond (acute inflammation) to the stimuli, followed by excluding the stimuli to repair the damages. Alternatively, if the exclusion is difficult, the damages are progressed to induce continuously tissue swelling (chronic inflammation). Inflammation is well known to be associated with several diseases, and various mediators are known to be associated with each step during the inflammation process, constituted with activation and interactions of various cells.

PLA(2) is a diverse class of enzymes, catalyzing preferentially the hydrolysis of the sn-2 acyl-ester of glycerophospholipids, that are major components of cell membranes, to liberate fatty acids. It is also well known that the PLA(2)s are responsible for deacylation-reacylation process required for cell membrane repair and maintenance, and the hydrolyzed products, as well as the further metabolites, are lipid mediators with strong diverse physiological activities. The liberated product, arachidonic acid with some activity as mediator, is further metabolized in respective inflammation-associated cells to prostagladins, thromboxanes, lipoxins, leukotrienes, etc., which induce characteristic physiological responses, respectively (Irvine, R., *Biochemical Journal* 204: 3–16 (1982).). The other product, lysophosphatidylcholine not only plays roles as mediator, but also is utilized as a precursor of platelet activating factor (hereinafter referred to as PAF). These lipid mediators play an essential role to maintain homeostasis of living organisms, however, when they produced to excessive amounts under sick conditions associated with inflammation, they could cause adversely effects. In fact, steroidal anti-inflammatory drugs and various non-steroidal anti-inflammatory drugs (hereinafter referred to as NSAID) are known to interfere with the arachidonic acid cascade, have been widely used in clinical therapy. As PLA(2) is positioned at the upstream of the arachidonic acid cascade and is believed to be the rate-limiting step in the generation of these lipid mediators, this enzyme has been expected to be the promising target for research and development of novel anti-inflammatory drugs (Glaser, K. B., *Advances in Pharmacology* 32: 31–66 (1995).).

Recently, numerous PLA(2)s have been identified and rapidly become a large superfamily consisted of more than 15 isozymes are subdivided into four groups, on the basis of the protein structures and the characteristics in the enzymatic activities(Dennis, E. A., *Trends in Biochemical Science*, 22: 1–2 (1997), and Balsinde, J. et al, *Annual Review of Pharmacology and Toxicology*, 39: 175–189 (1999), etc.). Among them, it is noted that only the particular isozymes are shown high specificity against arachidonyl-phospholipids, as well as the enzymatic activity of the particular isozymes are selectively enhanced in a case of inflammatory disorder. As the examples for such inflammation-associated PLA(2)s, type IV-cytosolic PLA(2) (hereinafter referred to as IV-cPLA(2); molecular weight 85 kDa) and the subtypes IIA, IID, V and X of secretory PLA(2) (hereinafter referred to as sPLA(2); molecular weight 14 kDa) may be exemplified. Among these, IV-cPLA (2) is particularly considered as the responsible isozyme for producing the lipid mediators in the inflammatory diseases, which is supported by findings from the 'knockout' (IV-cPLA(2)$^{-/-}$)mice (Uozumi, N. et al, *Nature* 390: 619–622 (1997), and Bonventre, J. V. et al, *Nature* 390: 622–625 (1997).). Therefore, the enhanced lipid mediators production under sick conditions could be suppressed by inhibiting IV-cPLA(2) activity, thereby facilitating remedy and/or prevention of the inflammatory diseases. Such diseases can be exemplified as following: anaphylaxis induced by various inflammatory stimuli, septic shock, fever and pain; respiratory diseases, such as bronchitis, pneumonia, and adult respiratory distress syndrome; digestive diseases, such as inflammatory intestine disorder, Crohn's disease, ulcerative colitis, hepatitis, and nephritis; cardiovascular diseases, such as vasculitis and arteriosclerosis; allergic inflammatory diseases, such as rhinitis, asthma and atopic syndromes; and auto-immune diseases such as rheumatism; ischemia/reperfusion injuries, such as cerebral infarction and myocardial infarction; nerve degenerative diseases, solar keratosis, psoriasis, and the like.

However, as no drug has been developed yet, which shows remedial effects in the clinical therapies by inhibiting the enzyme activity, it is desired to develop such a new drug that can specifically and comprehensively control the lipid mediators production in inflammatory diseases, with excellent therapeutic and preventive effects.

In WO97/05135, compounds represented by the following general formula;

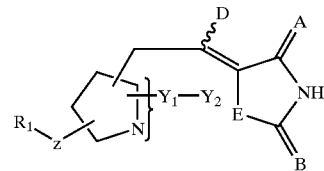

are disclosed as oxa(thia)zolidine derivatives having activity of inhibiting the PLA (2) activity. However, the compounds which show to have said inhibitory activity are limited to ones wherein the second and the fourth positions are substituted by either oxo or thio. Furthermore, in WO93/10789, 2-imino-4-oxothiazolidine derivative represented by the following chemical formula is disclosed.

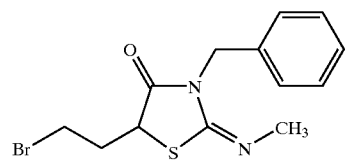

It is described in Jpn. Pat. Appln. KOKAI publication No. 63-41471 that the oxa(thia)zolidine derivatives related to the present invention have acaricidal activity. However, it is not known so far that those oxa(thia)zolidine derivatives have PLA(2) inhibitory activity or anti-inflammatory activity.

DISCLOSURE OF THE INVENTION

As described above, it is understood that the enhanced PLA(2) activity plays a major role in the progress of various inflammatory diseases. Therefore, an object of the present invention is to provide medicinal compositions which is effective to remedy the inflammatory sick condition and to cure or prevent the relevant disease, and novel compounds to be used for the medicinal composition.

As a result of the studies by the inventors of the present invention for aiming at achieving the aforementioned object, it is found out that the oxa(thia)zolidine derivatives, which had been known to have acaricidal activity, have been found out also having inhibitory activity on PLA(2), thereby reaching the present invention.

The present invention is constituted with the following aspects (1) through (12).

(1) A medicinal composition characterized by containing as the active ingredient either a compound represented by a general formula (1) or a pharmaceutically acceptable composite thereof;

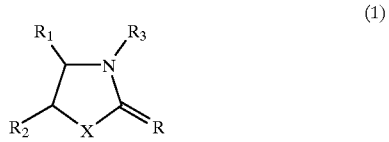

(1)

wherein X represents oxygen or sulfur, $R_1$ represents hydrogen, $C_{1-4}$ alkyl or $C_{1-4}$ haloalkyl, $R_2$ represents phenyl optionally substituted by $A_1$, naphthyl optionally substituted by $A_1$, 5 to 6-membered heterocyclic group optionally substituted by $A_1$ containing at least one heteroatom selected from a group consisting of oxygen, sulfur and nitrogen, quinolyl optionally substituted by $A_1$, or a group represented by a formula (2);

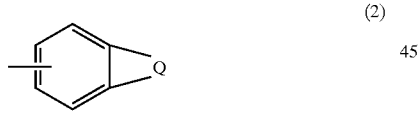

(2)

wherein Q represents —(CH$_2$)$_3$—, —(CH2)$_4$— or —OCH$_2$O—, $R_3$ represents hydrogen, $C_{1-4}$ alkyl optionally substituted by $A_2$, $C_{1-4}$ alkoxy optionally substituted by $A_2$, $C_{1-4}$ alkylcarbonyl optionally substituted by $A_2$, $C_{1-4}$ alkoxycarbonyl optionally substituted by $A_2$, $C_{2-4}$ alkenylcarbonyl optionally substituted by $A_2$, phenyliminomethyl optionally substituted by $A_3$, phenyl optionally substituted by $A_3$, anilino optionally substituted by $A_3$, or a group represented by the following formulae;

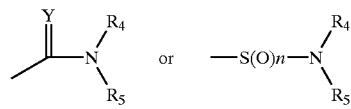

wherein Y represents oxygen or sulfur, $R_4$ represents hydrogen or $C_{1-4}$ alkyl, $R_5$ represents $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, benzoyl optionally substituted by $A_3$, anilino optionally substituted by $A_3$, $C_{1-6}$ alkoxycarbonyl optionally substituted by $A_2$, phenylsulfonyl optionally substituted by $A_3$, $C_{1-6}$ alkoxysulfonyl optionally substituted by $A_2$, mono- or di-($C_{1-6}$ alkyl)aminosulfonyl optionally substituted by $A_2$, or 5- to 7-membered heterocyclic group optionally substituted by $A_4$ containing at least one atom selected from a group consisting of oxygen, sulfur and nitrogen as a heteroatom, and n represents 0, 1 or 2, R represents oxygen, sulfur or a group represented by a formula of N—G, wherein G represents hydrogen, nitro, cyano, $C_{1-4}$ alkyl optionally substituted by $A_2$, $C_{1-4}$ alkoxy, $C_{1-4}$ alkylcarbonyl, phenyl optionally substituted by $A_3$, benzoyl optionally substituted by $A_3$, anilino optionally substituted by $A_3$, a group represented by a formula of NHCOR$_6$, wherein R$_6$ represents $C_{1-4}$ alkyl or phenyl optionally substituted by $A_3$, or a group represented by the following formula;

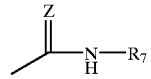

wherein Z represents oxygen or sulfur, $R_7$ represents $C_{1-4}$ alkyl, $C_{3-7}$ cycloalkyl optionally substituted by $A_4$, phenyl optionally substituted by $A_3$, benzoyl optionally substituted by $A_3$, or optionally substituted 5- to 6-membered saturated heterocyclic group, $A_1$ represents halogeno, amino, nitro, cyano, $C_{1-12}$ alkyl, $C_{2-6}$ alkenyl, $C_{1-4}$ haloalkyl, $C_{3-7}$ cycloalkyl, phenyl optionally substituted by halogeno, $C_{1-4}$ alkyl or $C_{1-4}$ haloalkyl, pyridyl, thienyl, $C_{1-4}$ alkoxy, methylenedioxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, benzyl, phenethyl, phenoxy, phenylthio, $C_{1-4}$ alkoxycarbonyl, $C_{1-4}$ haloalkoxycarbonyl, $C_{1-4}$ alkylcarbonyloxy, carbamoyl, or mono- or di-($C_{1-4}$ alkyl)carbamoyl, $A_2$ represents halogeno, $C_{1-4}$ alkoxy, $C_{1-4}$ alkoxy $C_{1-4}$ alkoxy, amino, mono- or di-($C_{1-4}$ alkyl)amino, $C_{1-4}$ alkylcarbonyloxy, $C_{1-4}$ alkoxycarbonyl, halo $C_{1-4}$ alkoxycarbonyl, $C_{1-4}$ alkylcarbamoyl, di-($C_{1-4}$ alkyl) carbonylamino, morpholino, phenyl, or pyridyl optionally substituted by halogeno, $A_3$ represents halogeno, hydroxy, oxo, mercapto, nitro, amino, cyano, $C_{1-4}$ alkyl, $C_{1-4}$ haloalkyl, pyridyl, $C_{1-4}$ alkoxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, $C_{1-4}$ alkylcarbonyl, $C_{1-4}$ alkoxycarbonyl, $C_{1-4}$ haloalkoxycarbonyl, carbamoyl, mono- or di-($C_{1-4}$ alkyl)carbamoyl, or $C_{1-4}$ alkoxycarbonyl $C_{1-4}$ alkylthio, and $A_4$ represents halogeno, hydroxy, oxo, $C_{1-4}$ alkyl, halo $C_{1-4}$ alkyl, $C_{1-4}$ alkoxy, $C_{1-4}$ alkylthio, halo $C_{1-4}$ alkoxy, halo $C_{1-4}$ alkylthio, $C_{1-4}$ alkoxy $C_{1-4}$ alkoxy, $C_{1-4}$ alkylsulfonyl, $C_{1-4}$ alkoxycarbonyl, or $C_{1-4}$ haloalkoxycarbonyl, provided that R is oxygen or sulfur, $R_3$ represents a group represented by the following formula;

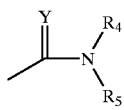

wherein Y, $R_4$ and $R_5$ are as defined above.

(2) Compounds represented by a general formula (1—1);

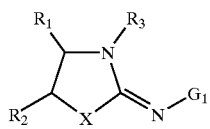

(1-1)

wherein X, $R_1$, $R_2$ and $R_3$ are as defined in the section (1) described above, $G_1$ represents nitro, cyano, $C_{1-4}$ alkylcarbonyl, benzoyl optionally substituted by $A_3$, $NHCOR_6$, wherein $R_6$ represents $C_{1-4}$ alkyl or phenyl optionally substituted by $A_3$, or a group represented by the following formula;

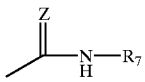

wherein Z and $R_7$ are as defined in the section (1) described above, and $A_3$ is as defined in the section (1) described above.

(3) An inhibitor of PLA(2) activity comprising as the active ingredient at least one selected from a group consisting of heterocyclic compounds represented by the general formula (1) and the pharmaceutically acceptable composites thereof.

(4) A use of a composition for a mammalian animals which requiring remedy for inflammatory diseases or disorders, where the composition is characterized by containing as the active ingredient at least one selected from a group consisting of heterocyclic compounds represented by the general formula (1) and the pharmaceutically acceptable composites thereof.

(5) A method to remedy or reduce inflammatory diseases or disorders, curing and/or preventing taking turn for the worth by administering a medicinal composition, which is comprising an effective dose of at least one selected from a group consisting of compounds represented by the general formula (1) and the pharmaceutically acceptable composites thereof to a mammalian requiring treatment.

(6) The method defined in the section (5) described above; wherein the inflammatory diseases or the disorders are any of anaphylaxis, allergic inflammation, asthma, rhinitis, bronchitis, pneumonia, and adult respiratory distress syndrome, inflammatory intestine disorder, Crohn's disease, ulcerative colitis, ischemia/reperfusion injuries, vasculitis, arteriosclerosis, hepatitis, nephritis, nerve degenerative diseases, arthritis, dermatitis, solar keratosis, psoriasis, septic shock and fever.

(7) The method defined in the section (5) described above, wherein the progress of the sick condition is due to inflammatory disease or disorder that is accompanied with the enhanced PLA(2) activity.

(8) The method defined in the section (5) described above, wherein the inflammatory disease or disorder is mediated by pro-inflammatory lipid mediators, such as arachidonic acid and the metabolites thereof, and/or lysophosphatidylcholines, and/or PAF.

(9) The method defined in the section (8) described above, wherein the pro-inflammatory lipid mediators are suppressed by the inhibitor of PLA(2) activity.

(10) A use of a heterocyclic derivative of the general formula (1) for manufacturing of a medicinal composition, which is used for reducing inflammatory and/or allergic sick condition and/or sick condition associated with immunity, and/or for the remedy of such diseases and disorders.

(11) A use of a composition as a medicine, where the composition contains as the active ingredient at least one selected from a group consisting of heterocyclic derivatives represented by the general formula (1) and the pharmaceutically acceptable composites thereof.

(12) A use of a composition as an anti-inflammatory drug, anti-allergic drug and/or immune controlling drug, where the composition contains as the active ingredient at least one selected from a group consisting of heterocyclic derivatives represented by the general formula (1) and the pharmaceutically acceptable composites thereof.

EMBODIMENTS FOR CARRYING OUT THE INVENTION

In the compounds according to the present invention, which are represented by the general formula (1), X represents oxygen or sulfur, $R_1$ represents hydrogen; $C_{1-4}$ alkyl selected from methyl, ethyl, propyl, isopropyl, butyl, i-butyl, sec-butyl and t-butyl; or $C_{1-4}$ haloalkyl, such as chloromethyl, fluromethyl, bromomethyl, dichloromethyl, trichloromethyl and pentafluromethyl, $R_2$ represents phenyl optionally substituted by $A_1$; naphthyl optionally substituted by $A_1$; 5- to 6-membered heterocyclic group containing at least one heteroatom selected from oxygen, sulfur and nitrogen, such as thienyl, furyl, tetrahydrothiapyranyl, 2H, 5H, 6-H-thiapyranyl, pyranyl, tetrahydropyranyl, pyridyl, pyrimdyl, imidazolyl, oxazolyl, and thiazolyl, optionally substituted by $A_1$; quinolyl optionally substituted by $A_1$; or a group represented by the following formula (2);

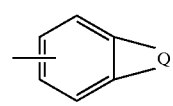

(2)

wherein Q represents a group represented by $-(CH_2)_3-$, $-(CH_2)_4-$ or $-OCH_2O-$, $R_3$ represents hydrogen; $C_{1-4}$ alkyl, such as methyl and ethyl, optionally substituted by $A_2$; $C_{1-4}$ alkoxy, such as methoxy, ethoxy and propoxy, optionally substituted by $A_2$; $C_{1-4}$ alkylcarbonyl, such as acetyl, ethylcarbonyl, propylcarbonyl and butylcarbonyl, optionally substituted by $A_2$; $C_{1-4}$ alkoxycarbonyl, such as methoxycarbonyl, ethoxycarbonyl, propoxycarbonyl and butoxycarbonyl, optionally substituted by $A_2$; $C_{2-4}$ alkenylcarbonyl, such as ethenylcarbonyl and allylcarbonyl, optionally substituted by $A_2$; phenylimino-methyl optionally substituted by $A_3$; phenyl optionally substituted by $A_3$; anilino optionally substituted by $A_3$; or a group represented by the following formulae;

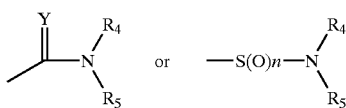

wherein Y represent oxygen or sulfur,

R$_4$ represents hydrogen, or C$_{1-4}$ alkyl such as methyl and ethyl,

R$_5$ represents C$_{1-6}$ alkyl, such as methyl and ethyl, optionally substituted by A$_2$; C$_{2-6}$ alkenyl, such as ethenyl and allyl, optionally substituted by A$_2$; C$_{2-6}$ alkynyl, such as ethynyl and propynyl, optionally substituted by A$_2$; C$_{1-6}$ alkoxy, such as methoxy, ethoxy and butoxy, optionally substituted by A$_2$; C$_{2-6}$ alkenyloxy, such as ethenyloxy and allyloxy, optionally substituted by A$_2$; mono- or di-(C$_{1-6}$ alkyl)amino, such as methylamino, dimethylamino and ethylamino, optionally substituted by A$_2$; C$_{3-7}$ cycloalkyl, such as cyclopropyl, cycloheptyl and cyclohexyl, optionally substituted by A$_4$; C$_{5-7}$ cycloalkenyl such as cyclohexenyl optionally substituted by A$_4$; phenyl optionally substituted by A$_3$; benzoyl optionally substituted by A$_3$; anilino optionally substituted by A$_3$; C$_{1-6}$ alkoxycarbonyl, such as methoxycarbonyl and ethoxycarbonyl, optionally substituted by A$_2$; phenylsulfonyl optionally substituted by A$_3$; C$_{1-6}$ alkoxysulfonyl such as methoxysulfonyl optionally substituted by A$_2$; mono- or di-(C$_{1-6}$ alkyl) aminosulfonyl, such as methylaminosulfonyl, dimethylaminosulfonyl and diethylaminosulfonyl, optionally substituted by A$_2$; or 5- to 7-membered heterocyclic group containing at least one selected from oxygen, sulfur and nitrogen as an heteroatom, optionally substituted by A$_4$, and n represents 0, 1 or 2, and R represents oxygen, sulfur or a group represented by a formula of N—G, wherein G represents hydrogen, nitro, cyano, C$_{1-4}$ alkyl optionally substituted by A$_2$, C$_{1-4}$ alkoxy, C$_{1-4}$ alkylcarbonyl, phenyl optionally substituted by A$_3$, benzoyl optionally substituted by A$_3$, anilino optionally substituted by A$_3$, NHCOR$_6$, wherein R$_6$ represents C$_{1-4}$ alkyl or phenyl optionally substituted by A$_3$, or a group represented by the following formula;

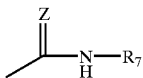

wherein Z represents oxygen or sulfur, R$_7$ represents C$_{1-4}$ alkyl, C$_{3-7}$ cycloalkyl optionally substituted by A$_4$, phenyl optionally substituted by A$_3$, benzoyl optionally substituted by A$_3$, or optionally substituted 5- to 7-membered heterocyclic group.

The 5- to 7-membered heterocyclic group in the definition for the group represented by R$_5$ and R$_7$ means a saturated or unsaturated heterocyclic group constituted by 5 to 7 atoms and containing at least one heteroatom selected from oxygen, sulfur and nitrogen. Particularly, the 5- to 7-membered heterocyclic group includes tetrahydrofuranyl, tetrahydrothienyl, pyrrolidinyl, pyrazolidinyl, imidazolidinyl, tetrahydropyranyl, tetrahydrothiapyranyl, piperidinyl, pyrimidinyl, pyridyl, and the like, and examples for the substituted "5- to 7-membered heterocyclic group" includes N-methylpiperidinyl, 2,6-dimethylmorpholino, 3-methyloxathianyl, 6-methoxytetrahydropyranyl, and the like.

In the definition for the groups represented by A$_1$, A$_2$, A$_3$ and A$_4$, the halogeno denotes fluoro, chloro, bromo, iodo and the like, the C$_{1-4}$ alkyl denotes a normal or branched chain alkyl having 1 to 4 carbon atoms, which specifically includes methyl, ethyl, propyl, isopropyl, n-butyl, i-butyl, s-butyl and t-butyl, the C$_{1-12}$ alkyl denotes pentyl, hexyl, dodecyl and the like in addition to said C$_{1-4}$ alkyls, the C$_{1-4}$ haloalkyl denotes chloromethyl, bromomethyl, trifluoromethyl and the like, the C$_{3-7}$ cycloalkyl means a cyclic saturated hydrocarbon containing 3 to 7 carbon atoms, which specifically includes cyclopropyl, cyclopentyl, cyclohexyl, cycloheptyl, and the like, the C$_{1-4}$ alkoxy denotes methoxy, ethoxy and the like, and the C$_{1-4}$ alkylthio denotes methylthio, ethylthio and the like, the C$_{1-4}$ alkoxy C$_{1-4}$ alkoxy denotes methoxymethy, ethoxymethyl, methoxyethyl and the like, the alkylsulfenyl denotes methylsulfenyl, ethylsulfenyl and the like, and the C$_{1-4}$ alkylsulfonyl denotes methanesulfonyl, ethanesulfonyl and the like, the mono- or di-(C$_{1-4}$ alkyl)amino denotes methylamino, dimethylamino, ethylamino, methylethylamino and the like, the C$_{1-4}$ haloalkoxy denotes chloromethoxy, bromomethoxy, trifluoromethoxy, chloroethoxy, fluoroethoxy and the like, the C$_{1-4}$ alkoxycarbonyl denotes methoxycarbonyl, ethoxycarbonyl and the like, the C$_{1-4}$ haloalkoxycarbonyl denotes chloromethoxycarbonyl, trifluoromethoxycarbonyl and the like, and C$_{1-4}$ alkylcarbonyloxy denotes acetoxy, ethylcarbonyloxy and the like, and the mono- or di-(C$_{1-4}$ alkyl)carbamoyl denotes methylcarbamoyl, ethylcarbamoyl, dimethylcarbamoyl, propylcarbamoyl, isopropylcarbamoyl and the like, provided that R is oxygen or sulfur, R$_3$ represents a group represented by the following formula;

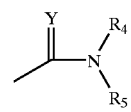

wherein Y, R$_4$ and R$_5$ are as defined above.

Among the compounds according to the present invention, the compounds in which R is a group represented by N—G$_1$ are novel compounds which have not been described in the previous references. Furthermore, among the compounds in which R is either oxygen or sulfur, most compounds in which R$_2$ is naphthyl optionally substituted by A$_1$, 5- to 6-membered heterocyclic groups optionally substituted by A$_1$, quinolyl optionally substituted by A$_1$, or a group represented by the formula (2), are novel compounds.

"The pharmaceutically acceptable composite" denotes a composite comprising the compound described above and an atoxic low-molecular compound those interact with ionic, hydrogen or coordinate bonds each other, at a particular combining ratio, and the compound should be liberated after the composite is solubilyzed in an aqueous solution. Specific examples for the pharmaceutically acceptable composite include salts with ionic materials such as hydrochlorides, organic acids, amino acids and the like, and solvates such as hydrates.

Now, the process for manufacturing the compounds according to the present invention is explained below.

Among the compounds represented by the general formula (1), the compounds except the novel compounds represented by the general formula (1—1) and the pharmaceutically acceptable composite thereof may be prepared according to the preparation process disclosed in Jpn. Pat. Appln. KOKAI Publication No. 63-41471, etc.

The compounds represented by the general formula (1—1) may be prepared according to the following process.

Preparation Process 1: The compounds wherein $G_1$ is either cyano or nitro, and X is oxygen:

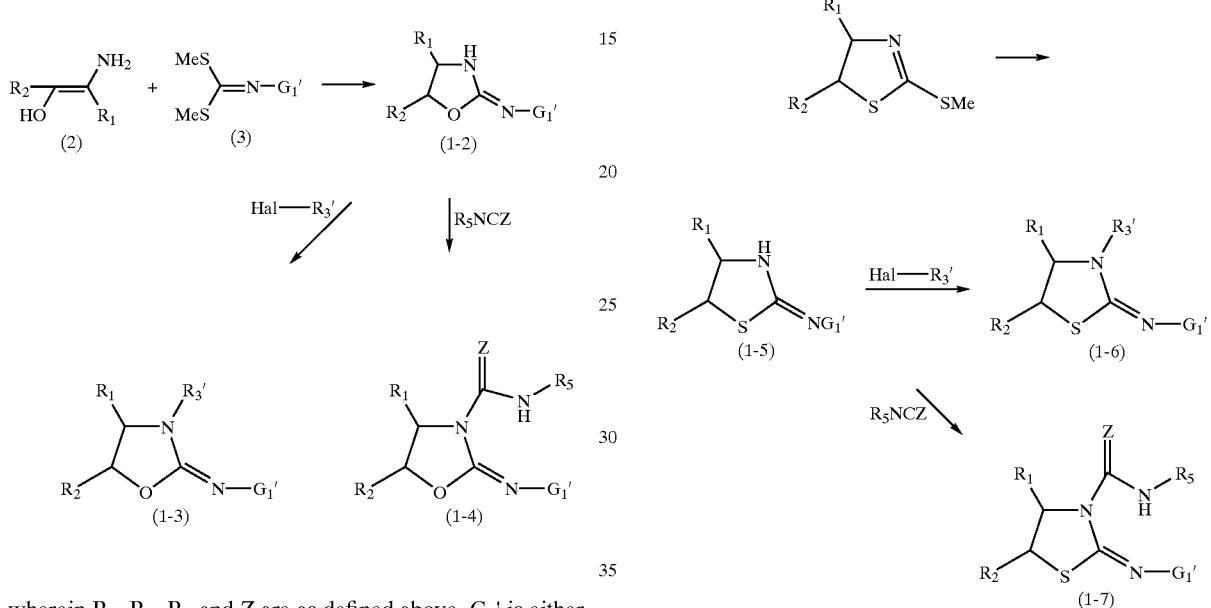

wherein $R_1$, $R_2$, $R_5$ and Z are as defined above, $G_1'$ is either cyano or nitro, and $R_3'$ represents the same groups represented by $R_3$ except groups represented by a formula of $Y'NR_4R_5$ wherein $Y'$ represents C=O or C=S, and $R_4$ and $R_5$ are as defined above.

Preparation Process 2: The compounds wherein $G_1$ is either cyano or nitro and X is sulfur may be prepared according to the process described in Jpn. Pat. Appln. KOKAI Publication No. 63-41471.

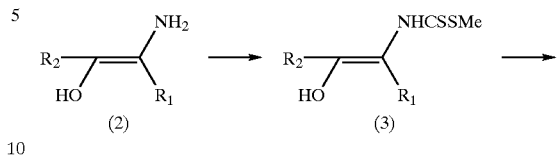

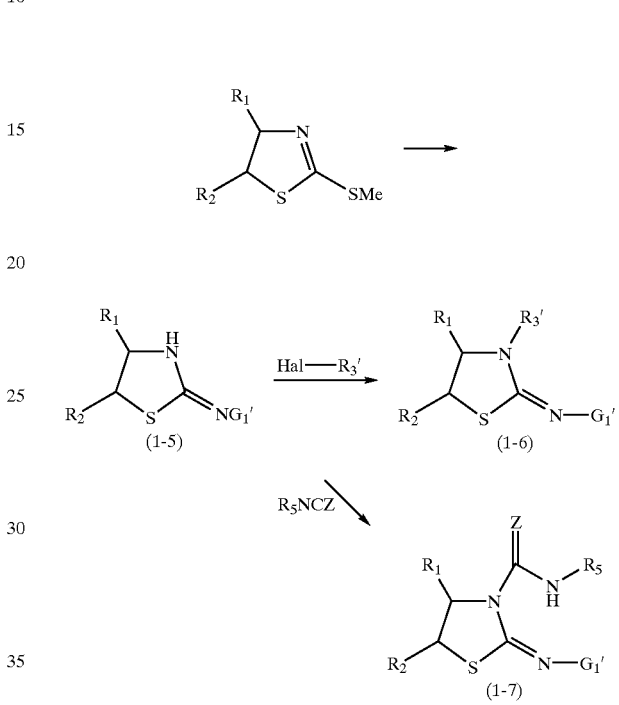

Preparation process 3: The compounds wherein $G_1$ and/or $R_3$ is $Y'NR_4R_5$ may be prepared according to the following reaction formulae.

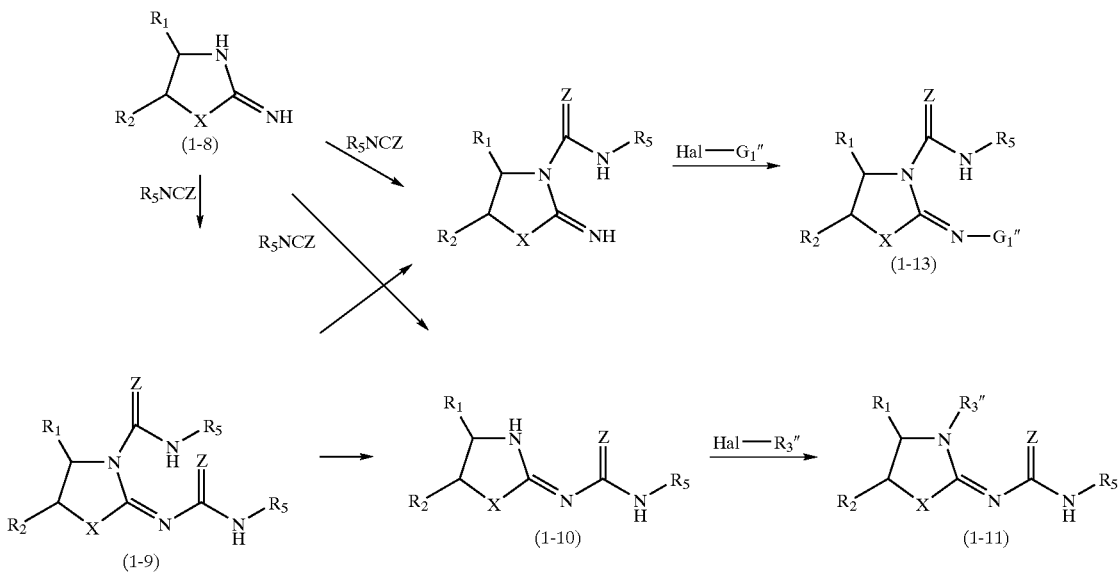

The reaction of the compound (2) and the compound (3) in the preparation process 1 may be carried out in an organic solvent for 1 to several hours at the temperature ranging from room temperature to the boiling point of the used solvent. As the organic solvent for the above reaction, alcohols, dioxane, THF, DMF and the like may be used.

The respective reactions of the compounds (1–2), (1–5), (1–10) and (1–12) with a halide are carried out in an organic solvent in the presence of a base for 1 to scores of hours at the temperature ranging from −20° C. to the boiling point of the used solvent, and preferably from 0° C. to 50° C. As the organic solvent for these reactions, DMF, THF, DMSO, alcohols and the like may be used. As the base for these reactions, sodium hydride may be used, or any of alkoxides, triethylamine, 1,8-diazabicyclo(5,4,0)undecene-7 (hereinafter referred to as DBU) and the like may be used as well.

The respective reactions of the compounds (1–2), (1–5) and (1–8) with either a cyanate or an isothiocyanate represented by a formula of $R_5NCZ$ may be carried out in an organic solvent in the presence of a base for 1 to scores of hours at the temperature ranging from −20° C. to 60° C., and preferably from 0° C. to room temperature. As the organic solvent for these reactions, DMF, DMSO, THF, dioxane, benzene, ethyl acetate and the like may be used. As the base for these reactions, triethylamine, DBU, Pyridine and the like may be used.

After each reaction represented above, work-up may be employed as conventionally to obtain the objective compound.

The chemical structures of the compounds according to the present invention were determined by means of MASS, NMR, etc.

The chemical structures of the compounds according to the present invention were determined by means of MASS, NMR, etc.

The compounds represented by the general formula (1) respectively include their structural isomers associated with at least the fourth and fifth positions of the oxa(thia)zolidine portion and their optical isomers. In addition, when $R_3$ in the compound is hydrogen, the following tautomers may be arisen.

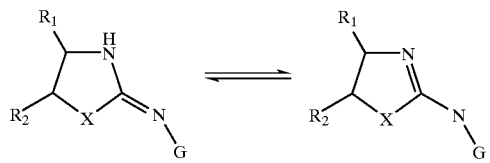

It is to be noted that each of the compounds according to the present invention is not limited to the specific isomers, namely compounds may include all possible isomers as well as possible racemic modifications. Furthermore, depending on circumstances, the compounds according to the present invention also may include the prodrugs and the metabolites of the compounds indicated above.

Now, the medicinal composition according to the present invention and the use thereof are explained below.

The compound represented by the general formula (1) or the pharmaceutically acceptable composite thereof may be administered to humans and animals either directly or together with common carriers for pharmaceutical formulations. For applying the composite, the administration route is not limited, and either route of systemic administration or topical application, i.e. non-systemic administration, may be selected appropriately upon necessity. Examples of the drug form for medical treatment include pharmaceutical formulations for oral administration such as tablets, capsules, granules, and powders, drinkable solutions, troches and the like; and parenteral solutions or suspensions for intravenous injection, intramuscular injection, subcutaneous injection and the like. In addition, other administration routes, such as through rectum with suppositories, and through lung (through nose or inhalation through mouth) with aerosols, powder inhalants, etc. may be employed for applying the medicinal composition according to the present invention. As pharmaceutical formulations suitable for the topical application to penetrate the active ingredient into the inflammatory regions through skins and mucosae, solutions, liniments, creams, emulsions, ointments and pastes, as well as drops suitable for the treatment to eyes, ears and noses may be exemplified. There is no limit for the amount of the active ingredient to be applied, and therefore, the dose may be appropriately selected in a wide range depending upon the administration routes, the applied compounds, and the treated patients, namely to humans or animals. In order to exert the desired medicinal effectiveness, the compound of the present invention is preferably administered at a daily dose of 0.01–100 mg per kg body weight, with or without dividing the dose into several times. For the pharmaceutical formulations, it is preferable to contain the active ingredient in unit dosage form at a dose of 0.01 to 1,000 mg.

The pharmaceutical formulations for oral administration comprising the compound according to the present invention, such as tablets, capsules, granules and drinkable solutions, may be prepared according to any of the conventional methods. More specifically, the tablets may be prepared by mixing the compound represented by the general formula (1) or the pharmaceutically acceptable composite thereof with pharmaceutical fillers, such as starch, lactose, gelatin, magnesium stearate, talc, gum arabic, and the like, and forming into tablets. The capsules may be prepared by mixing the compound represented by the general formula (1) or the pharmaceutically acceptable composite thereof with an inactive pharmaceutical filler or diluent, and then charged into capsules made of hard gelatin, soft capsules, or the like to. The medicated syrups and elixirs for oral administration may be prepared by mixing the compound represented by the general formula (1) or the pharmaceutically acceptable composite thereof with a sweetener such as sucrose, an antiseptic such as Methylparaben and Propylparaben, a coloring agent, a flavor, and the like. Further, the parenteral pharmaceutical formulations of the compound of the present invention may be prepared according to any of the conventional processes. For example, a parenteral pharmaceutical formulation may be prepared by dissolving the compound represented by the general formula (1) or the pharmaceutically acceptable composite thereof with a sterilized liquid carrier. As the liquid carrier, water or saline solution may be preferably used. In order to provide the solution with a desired transparency, stability and congeniality for the parenteral use, approximately 0.1 to 1,000 mg of the active ingredient may be dissolved in either water or an organic solvent, and further dissolved with polyethylene glycol having a molecular weight of 200 to 5,000. For the preparation of the solution, it is preferable that a lubricant, such as polyvinylpyrrolidone, polyvinyl alcohol, sodium carboxymethyl cellulose, and methyl cellulose, is incorporated therein. Furthermore, a bactericide such as benzyl alcohol, phenol and Thimerosal, and a fungicide may be incorporated into the solution, in addition, an osmotic pressure conditioner, such as sucrose and sodium chloride, a local anesthetic, a stabilizer, a buffer agent and the like may be incorporated into the solution upon necessity. More stable pharmaceutical formulation for parenteral use may be provided by removing moisture in the frozen preparation following to the filling, by means of freeze-drying technique known in the field. Accordingly, it is also possible to resolve the lyophilized powder thereof to prepare a pharmaceutical formulation just before the use.

BEST MODE FOR CARRYING OUT THE INVENTION

Now, the present invention is further explained with reference to the examples for the pharmaceutical formulations comprising the compound according to the present invention. However, it should be noted that the following examples are only for the purpose of illustrating the present invention, and that the present invention is not limited to the following examples.

PHARMACEUTICAL FORMULATION EXAMPLE 1

Tablets

| Compositions | Amount (g) |
| --- | --- |
| Compound of the present invention | 5 |
| Lactose (The Pharmacopoeia of Japan) | 50 |
| Corn starch (The Pharmacopoeia of Japan) | 25 |
| Crystalline cellulose (The Pharmacopoeia of Japan) | 25 |
| Methyl cellulose (The Pharmacopoeia of Japan) | 1.5 |
| Magnesium stearate (The Pharmacopoeia of Japan) | 1 |

A compound of the present invention, lactose, corn starch and crystalline cellulose were incorporated thoroughly. The mixture was formed into the granules with 5% aqueous solution of methyl cellulose, and the granules were passed through a sieve of 300 mesh and then dried carefully. The dried granules were incorporated with magnesium stearate and then prepared into tablets according to the conventional method to obtain 1,000 tablets.

PHARMACEUTICAL FORMULATION EXAMPLE 2

Capsules

| Compositions | Amount (g) |
| --- | --- |
| Compound of the present invention | 10 |
| Lactose (The Pharmacopoeia of Japan) | 80 |
| Starch (The Pharmacopoeia of Japan) | 30 |
| Talc (The Pharmacopoeia of Japan) | 5 |
| Magnesium stearate | 1 |

(The Pharmacopoeia of Japan)

The compositions recited above were incorporated and crushed into fine particulates. The particulates of the mixture were then stirred thoroughly so as to obtain the homogenous mixture. The mixture was then charged into capsules made of gelatin for oral administration use to obtain 1,000 pieces of two-pieces type gelatin capsules.

PHARMACEUTICAL FORMULATION EXAMPLE 3

Solution for Injection

| Compositions | Amount (g) |
| --- | --- |
| Compound of the present invention | 1 |
| Polyethylene glycol 4000 (The Pharmacopoeia of Japan) | 0.3 |
| Sodium chloride (The Pharmacopoeia of Japan) | 0.9 |
| Polyoxyethylene sorbitan monooleate (The Pharmacopoeia of Japan) | 0.4 |
| Sodium metabisulfite (The Pharmacopoeia of Japan) | 0.1 |
| Methylparaben (The Pharmacopoeia of Japan) | 0.18 |
| Propylparaben (The Pharmacopoeia of Japan) | 0.02 |
| Distilled water for injection use | Appropriate |
| (Final volume) | 100 (ml) |

The Parabens, sodium metabisulfite and sodium chloride were dissolved with approximately half of the final volume of distilled water for injection use at 80° C. while stirring. Then, the obtained solution was cooled down to 40° C. The compound of the present invention, and subsequently polyethylene glycol and polyoxyethylene sorbitan monooleate were added to the solution and dissolve therewith. Next, the rest portion of the distilled water was added into the solution so as to adjust the volume to the final volume mentioned. The solution was then filtered through an appropriate filter to sterilize to obtain the pharmaceutical formulation of aqueous solution suitable for parenteral use.

PHARMACEUTICAL FORMULATION EXAMPLE 4

Ointment

| Compositions | Amount (g) |
| --- | --- |
| Compound of the present invention | 0.1 |
| White soft paraffin | 10 |

The compound of the present invention was incorporated into the base material so as to be homogeneous therein.

PHARMACEUTICAL FORMULATION EXAMPLE 5

Aerosol

| Compositions | Amount (g) |
| --- | --- |
| Compound of the present invention | 0.25 |
| Ethanol | 29.75 |
| Propelant 22 (Chlorodifluoromethane) | 70 |

The compound of the present invention was incorporated into ethanol and then added with 1 part of Propelant 22 to obtain a mixture. The mixture was then cooled down to −30° C. and then placed in a charging apparatus. Next, an amount of the mixture required for a administration was transferred into a stainless container and was diluted with the rest portion of the Propelant 22 to prepare the solution for aerosol. The stainless container was then mounted with a valve unit to be ready for the administration.

PHARMACEUTICAL FORMULATION EXAMPLE 6

Dry Powder for Inhalation

| Compositions | Amount (g) |
|---|---|
| Compound of the present invention | 5 |
| Lactose | 95 |

The compound of the present invention was mixed with lactose to obtain a homogeneous mixture. The mixture was then charged into an inhaler for dry powder.

PHARMACEUTICAL FORMULATION EXAMPLE 7

Suppositories

| Compositions | Amount (g) |
|---|---|
| Compound of the present invention | 0.225 |
| Saturated fatty acid glyceride | 2.000 |

The compound of the present invention was passed through No. 60 mesh U.S. sieve and then suspended in saturated fatty acid glyceride having been melted beforehand with minimum heat. The mixture was charged into a molding for suppositories with the indication capacity of 2 g and then cooled.

Although the compounds represented by the general formula (1) or the pharmaceutically acceptable composites thereof show to have strong inhibitory activity on the liberation of arachidonic acid during inflammatory reaction, they have very weak inhibitory activity on the enzymatic hydrolysis due to secretary type IB-PLA(2) of porcine pancreas (hereinafter referred to as IB-sPLA(2); molecular weight 14 kDa) when using a phospholipid, of which carbon in the oleic acid substituent at the second position being labeled with a radioactive isotope, as the substrate. From this reason, an advanced safety can be expected for the compounds represented by the general formula (1) and the pharmaceutically acceptable composites thereof.

Since a part of the compounds of the present invention also shows hypolipemic activity by the oral administration, the compounds may be useful as anti-arteriosclerosis drugs.

Furthermore, a part of the compounds of the present invention has herbicidal, insecticidal, acaricidal and/or fungicidal activities as well, and they can be used as pesticides. In particular, an excellent performance can be expected, as a drug provided by the compounds which additionally have inhibitory activity against fungi that causes infectious diseases to mammalian animals, such as pneumonia by an opportunistically fungus infection.

Among the compounds of the present invention, represented by the general formula (1), the compounds in which $R_3$ is $C(=Y)NHR_5$ are particularly excellent in the activity as the aforementioned drugs, and the compounds in which $R_5$ is tetrahydrofuranyl or tetrahydropyranyl are specially useful as said drugs.

Now, the present invention is further explained in detail with reference to the examples described below. However, it should be noted that the following examples are only for the purpose of illustrating the present invention, and the present invention is not limited to the following examples.

EXAMPLE 1

Preparation of trans-5-(4-chlorophenyl)-4-methyl-2-nitroiminooxazolidine 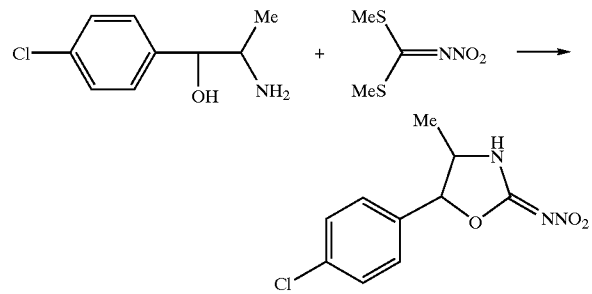 1.8 g of threo2-amino-1-(4-chlorophenyl)propanol and 1.7 g of dimethyl N-nitrodithioiminocarbonate were added into 20 ml of ethanol, and the mixture was refluxed for two hours. After the completion of the reaction, the reaction solution was condensed under reduced pressure, and the oily product obtained was purified by column chromatography to give 1.8 g of the title compound.

EXAMPLE 2

Preparation of trans-5-(4-chlorophenyl)-4-methyl-3-(2-chloro-5-pyridylmethyl)-2-nitroiminooxazolidine 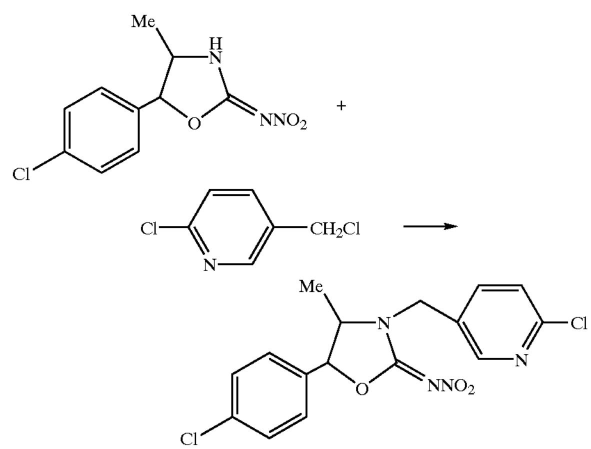 1.0 g of trans-5-(4-chlorophenyl)-4-methyl-2-nitroiminooxazolidine obtained in Example 1 and 0.2 g of 60% sodium hydride were added into 20 ml of DMF. 0.7 g of 2-chloro-5-chloromethylpyridine was added gradually to the mixture with stirring on cooling. Then, the mixture was further stirred for 6 hours at 70° C., followed by pouring the reaction mixture into ice water. The solution was extracted with ethyl acetate, and the organic layer was dried and then condensed under reduced pressure. The oily product obtained was purified by column chromatography to give 0.5 g of the title compound.

EXAMPLE 3

Preparation of trans-2-cyclohexylcarbamoylimino-3-cyclohexylcarbamoyl-4-methyl-5-(4-methylphenyl)thiazolidine

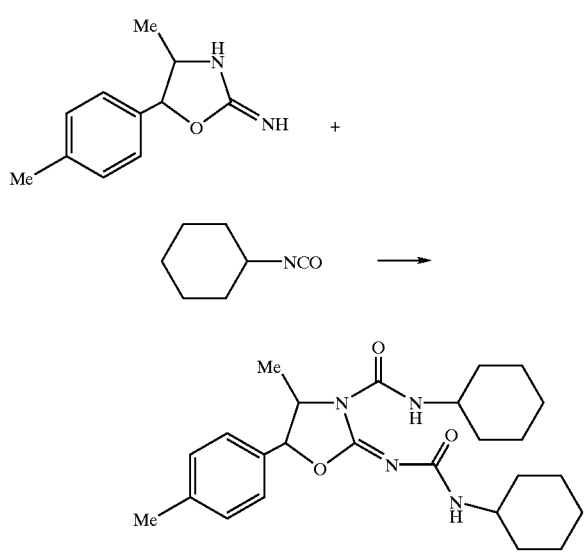

1.0 g of trans-2-imino-4-methyl-5-(4-methylphenyl)thiazolidine was dissolved in 20 ml of benzene. To the solution were added 1.3 g of cyclohexylisocyanate and one drop of triethylamine, respectively. The mixture was stirred for an hour at room temperature and refluxed for further an hour. The reaction solution was condensed under reduced pressure. The oily product obtained was purified by column chromatography to give 1.1 g of the title compound.

EXAMPLE 4

Preparation of trans-5-(4-methylphenyl)-4-methyl-2-cyclohexylcarbamoyliminothiazolidine

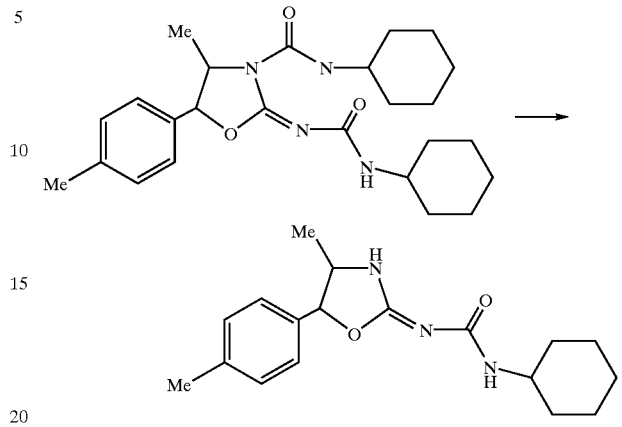

9.3 g of trans-2-cyclohexylcarbamoyl-4-methyl-5-(4-methylphenyl)thiazolidine was added into a mixture of 70 ml of ethanol and 70 ml of 3N hydrochloric acid, and the mixture was refluxed for 2 hours. The reaction mixture was neutralized with 5% aqueous solution of sodium hydroxide and extracted with ethyl acetate. The extract was washed with water, dried, and condensed under reduced pressure to give an oily product, which was purified by column chromatography to yield 5.4 g of the title compound.

The representative compounds usable in the present invention including the compounds prepared in the Examples described above are presented in Tables 1 and 2. The abbreviations and the reference symbols in the tables have the following meanings, respectively.

Me: methyl, Et: ethyl, Pr: propyl, Bu: butyl, Pn: pentyl, Hex: hexyl, Hep: heptyl, Allyl: allyl, Ac: acetyl, Ph: phenyl, Naph: naphthyl, Bn: benzyl, Bz: benzoyl, THF: tetrahydrofuranyl, Pyr: pyrrolidinyl, Dxln: 1,3-dioxolanyl, Im: imidazolyl, THP: tetrahydropyranyl, Py: pyridyl, Pip: piperidyl, Dxn: 1,3-dioxanyl, Morph: morpholinyl, pymd: pyrimidinyl, n: normal, i: iso, s: secondary, t: tertiary, c; cyclo.

TABLE 1

| Compound No. | X | $R_1$ | $R_2$ | $R_3$ | G | $R_1/R_2$ | Physical Constant [ ]:Melting Point ° C. |
|---|---|---|---|---|---|---|---|
| 1-1 | S | Me | 4-Me-Ph | —CONH-cHex | H | cis | [180–182] |
| 1-2 | S | Me | Ph | —CONH-cHex | H | trans | Oily substance*1 |
| 1-3 | S | Me | 4-Me-Ph | —CONH-cHex | H | trans | [116–118.5] |
| 1-4 | S | Me | 4-Cl-Ph | —CONH-cHex | H | trans | [111.5–112.5] |
| 1-5 | S | Me | 4-Cl-Ph | (pyridyl-CH2 with Cl) | CN | trans | $n_D^{25}$ 1.5994 |
| 1-6 | S | Me | 4-Cl-Ph | —CONH-cHex | CN | trans | |
| 1-7 | S | Me | 4-Cl-Ph | —SO₂NHMe | CN | trans | |

TABLE 1-continued

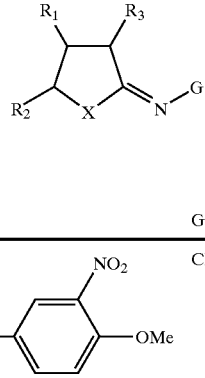

| Compound No. | X | $R_1$ | $R_2$ | $R_3$ | G | $R_1/R_2$ | Physical Constant [ ]:Melting Point ° C. |
|---|---|---|---|---|---|---|---|
| 1-8 | S | Me | 4-Cl-Ph | 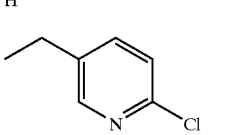 | CN | trans | |
| 1-9 | S | Me | 4-Cl-Ph | —CONH-2-THP | CN | trans | |
| 1-10 | O | Me | 4-Cl-Ph | H | $NO_2$ | trans | [123–126] |
| 1-11 | S | Me | 4-Cl-Ph | H | $NO_2$ | trans | [161–164] |
| 1-12 | O | Me | 4-Cl-Ph | 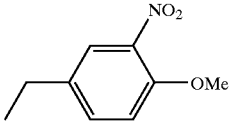 | $NO_2$ | trans | $n_D^{25.5}$ 1.5989 |
| 1-13 | S | Me | 4-Cl-Ph | —CONH-cHex | $NO_2$ | trans | |
| 1-14 | O | Me | 4-Cl-Ph | —$SO_2NMe_2$ | $NO_2$ | trans | [160–162] |
| 1-15 | S | Me | 4-Cl-Ph | —$SO_2NHMe$ | $NO_2$ | trans | |
| 1-16 | S | Me | 4-Cl-Ph | —$SO_2NHPh$ | $NO_2$ | trans | |
| 1-17 | S | Me | 4-Cl-Ph | 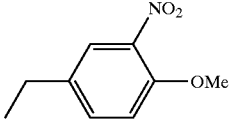 | $NO_2$ | trans | |
| 1-18 | S | Me | 4-Cl-Ph | —CONH-2-THP | $NO_2$ | trans | |
| 1-19 | O | Me | 4-Cl-Ph | H | Me | trans | [127–129] |
| 1-20 | O | Me | 4-Cl-Ph | —CONH-cHex | Me | trans | $n_D^{21}$ 1.5511 |
| 1-21 | O | Me | 4-Me-Ph | —CONH-cHex | Me | trans | $n_D^{22.5}$ 1.5409 |
| 1-22 | O | Me | 4-Me-Ph | —CONH-2-THP | Me | trans | $n_D^{22}$ 1.5392 |
| 1-23 | S | Me | 4-Me-Ph | —CONH-2-THP | Me | trans | |
| 1-24 | O | Me | 4-Me-Ph | —CONHPh | Me | trans | [87–95] |
| 1-25 | O | Me | 4-Me-Ph | —CONH-(4-Cl-Ph) | Me | trans | [106–109] |
| 1-26 | O | Me | 4-Me-Ph | —CONH-cHex | Me | trans | [120–123] |
| 1-27 | O | Me | 4-Me-Ph | —CONH-cHex | Et | trans | $n_D^{21}$ 1.5386 |
| 1-28 | O | Me | 4-Cl-Ph | —CONH-cHex | i-Pr | trans | [69–72] |
| 1-29 | O | Me | 4-Me-Ph | —CONH-cHex | t-Bu | trans | [98–100] |
| 1-30 | O | Me | 4-Me-Ph | —CONH-(4-Cl-Ph) | t-Bu | trans | [132–133] |
| 1-31 | S | Me | 4-Cl-Ph | H | t-Bu | trans | [215–218] |
| 1-32 | O | Me | 4-Me-Ph | —CONH-cHex | t-Bu | trans | [107–110] |
| 1-33 | O | Me | 4-Me-Ph | —CONH-(4-Cl-Ph) | t-Bu | trans | [137–140] |
| 1-34 | O | Me | 4-Me-Ph | —CONH-cHex | $CH_2CHCl$ | trans | $n_D^{25}$ 1.5265 |
| 1-35 | S | Me | 4-Me-Ph | H | $CH_2COOEt$ | trans | [184] |
| 1-36 | S | Me | 4-Cl-Ph | —CONH-cHex | $CH_2COOEt$ | trans | |
| 1-37 | S | Me | 4-Me-Ph | Me | $CH_2COOEt$ | trans | |
| 1-38 | S | Me | 4-Cl-Ph | H | cHex | trans | [133–135] |
| 1-39 | S | Me | 4-Cl-Ph | H | OEt | trans | [83–86] |
| 1-40 | S | Me | 4-Cl-Ph | COMe | OEt | trans | $n_D^{23.5}$ 1.5719 |
| 1-41 | S | Me | 4-Cl-Ph | $COCH=CH_2$ | OEt | trans | $n_D^{21.5}$ 1.5782 |
| 1-42 | S | Me | Ph | $CH_2CH(Ph)OCOMe$ | COMe | trans | [154–155] |
| 1-43 | S | Me | Ph | —CONH-cHex | COMe | trans | [156–158] |
| 1-44 | S | Me | Ph | —CONH-2-THP | COMe | trans | |
| 1-45 | S | Me | 4-Cl-Ph | 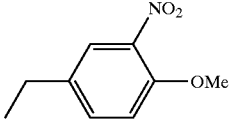 | COMe | trans | |
| 1-46 | S | Me | Ph | —CONH-cHex | COiPr | trans | |
| 1-47 | S | Me | Ph | —CONH-2-THP | COiPr | trans | |
| 1-48 | S | Me | 4-Me-Ph | —CONH-cHex | $COCH_2Cl$ | trans | [128–130] |

TABLE 1-continued

| Compound No. | X | $R_1$ | $R_2$ | $R_3$ | G | $R_1/R_2$ | Physical Constant [ ]:Melting Point °C. |
|---|---|---|---|---|---|---|---|
| 1-49 | S | Me | 4-Me-Ph | —CONH-cHex | COCH=CH$_2$ | trans | [158–159] |
| 1-50 | S | Me | 4-Me-Ph | —CONH-cHex | COOMe | trans | [172–178] |
| 1-51 | S | Me | 4-Me-Ph | —CONH-cHex | COOnBu | trans | [136–137] |
| 1-52 | S | Me | 4-Me-Ph | —CONH-cHex | COOPh | trans | Oily substance |
| 1-53 | S | Me | 4-Cl-Ph | H | Ph | trans | [150–151.5] |
| 1-54 | S | Me | Ph | H | Ph | trans | [136–137] |
| 1-55 | S | Me | Ph | H | 2,6-diMe—Ph | trans | [152–153] |
| 1-56 | S | Me | Ph | H | 4-Cl—Ph | trans | [187–188] |
| 1-57 | S | Me | 4-Cl—Ph | H | 2-Me—Ph | trans | [119–124] |
| 1-58 | S | Me | 4-Cl—Ph | H | 4-Cl—Ph | trans | [157–159] |
| 1-59 | S | Me | 4-Cl—Ph | H | 4-Me—Ph | trans | [163–165] |
| 1-60 | S | Me | 4-Cl—Ph | H | 4-CF$_3$O—Ph | trans | [119–120] |
| 1-61 | S | Me | 4-Cl-Ph | —CONHEt | 4-CF$_3$O—Ph | trans | $n_D^{25.5}$ 1.5586 |
| 1-62 | S | Me | 4-Cl-Ph | —CONH-(4-Cl—Ph) | 4-CF$_3$O—Ph | trans | [131–132] |
| 1-63 | S | Me | 4-Cl-Ph | —CONH-(4-NO$_2$—Ph) | 4-CF$_3$O—Ph | trans | |
| 1-64 | S | Me | 4-Cl-Ph | —CONH-(4-OMe—Ph) | 4-CF$_3$O—Ph | trans | |
| 1-65 | S | Me | 4-Cl-Ph | —CONH-(4-SO$_2$Me—Ph) | 4-CF$_3$O—Ph | trans | |
| 1-66 | S | Me | 4-Cl-Ph | —C=N-(2-Me-4-Cl—Ph) | 2-Me-4-Cl—Ph | trans | [55–57] |
| 1-67 | O | Me | 4-Me-Ph | —CONH-cHex | 2-Me-4-Cl—Ph | trans | [160–162] |
| 1-68 | O | Me | 4-Me-Ph | —CONH-cHex | 2-Me-4-Cl—Ph | trans | $n_D^{26}$ 1.5865 |
| 1-69 | O | Me | 4-Me-Ph | —CONH-cHex | Ph | trans | $n_D^{25.5}$ 1.5765 |
| 1-70 | O | Me | 4-Me-Ph | —CONH-(4-Cl-Ph) | 2-Me-4-Cl-Ph | trans | [199–201] |
| 1-71 | S | Me | 4-Cl-Ph | —CONH-cHex | Ph | trans | [116.5–118] |
| 1-72 | S | Me | 4-Cl-Ph | H | —CO-2,6-diF-Ph | trans | [114–116] |
| 1-73 | O | Me | 4-Me-Ph | H | —CO-(2-Me-6-Cl-Ph | cis | [104–106] |
| 1-74 | S | Me | 4-Cl-Ph | —CONH-cHex | CO-Ph | trans | |
| 1-75 | S | Me | 4-Cl-Ph | H | NHPh | trans | [145–146] |
| 1-76 | S | Me | 4-Cl-Ph | —CONH-(4-Cl-Ph) | NHPh | trans | [57–59] |
| 1-77 | S | Me | 4-Cl-Ph | —CONHEt | NHPh | trans | [50–52] |
| 1-78 | S | Me | Ph | H | NHPh | trans | [159.5]dec |
| 1-79 | S | Me | Ph | —CONH-cHex | NHPh | trans | |
| 1-80 | S | Me | Ph | H | NHCOPh | cis | [199–201] |
| 1-81 | S | Me | Ph | —CONH-2-THP | NHCOPh | trans | |
| 1-82 | S | Me | Ph | —CONH-cHex | NHCOPh | trans | |
| 1-83 | S | Me | Ph | H | NHCOPh | trans | |
| 1-84 | S | Me | 4-Cl-Ph | 4-Cl-Ph | —CONH-cHex | trans | [134–136.5] |
| 1-85 | S | Me | 4-Cl-Ph | 4-Me-Ph | —CONH-cHex | trans | [122.5–124.5] |
| 1-86 | S | Me | 4-Cl-Ph | H | —CONH-cHex | trans | $n_D^{26}$ 1.5547 |
| 1-87 | S | Me | 4-Cl-Ph | 4-Cl-Ph | —CONH(4-Cl-Ph) | trans | [115–117] |
| 1-88 | 5 | Me | 4-Cl-Ph | OEt | —CONHPh | trans | $n_D^{20.5}$ 1.6142 |
| 1-89 | S | Me | 4-Cl-Ph | 2-Me-4-Cl-Ph | —CONH-cHex | trans | $n_D^{19}$ 1.5632 |
| 1-90 | S | Me | 4-Cl-Ph | 4-Me-Ph | —CONH-cHex | trans | [70–71] |
| 1-91 | S | Me | 4-Cl-Ph | 2,4-diCl-Ph | —CONH-cHex | trans | $n_D^{25.5}$ 1.5586 |
| 1-92 | S | Me | 4-Cl-Ph | 2-Me-4-Cl-Ph | —CONH-cHex | trans | [119–120] |
| 1-93 | S | Me | 4-Cl-Ph | 2-Me-4-Cl-Ph | —CONH-Et | trans | [117–119] |
| 1-94 | S | Me | 4-Cl-Ph | 2-Me-4-Cl-Ph | —CONH-(4-Cl-Ph) | trans | $n_D^{25}$ 1.5891 |
| 1-95 | S | Me | 4-Cl-Ph | 2,4-diMe-Ph | —CONH-(4-Cl-Ph) | trans | $n_D^{25.5}$ 1.5796 |
| 1-96 | S | Me | 4-Cl-Ph | Ph | —CONH-cHex | cis | $n_D^{25.5}$ 1.5697 |
| 1-97 | S | Me | 4-Cl-Ph | 2-Me-4-Cl-Ph | —CONH-cHex | cis | [79–81] |
| 1-98 | S | Me | 4-Cl-Ph | 4-Cl-Ph | —CONH-cHex | cis | [132–133] |
| 1-99 | S | Me | 4-Cl-Ph | 2,4-diCl-Ph | —CONH-cHex | cis | [80–82] |
| 1-100 | S | Me | 4-Cl-Ph | 2,4-diMe-Ph | —CONH-cHex | cis | [78–80] |
| 1-101 | S | Me | 4-Cl-Ph | Me | —CONH-cHex | cis | $n_D^{27}$ 1.5658 |
| 1-102 | S | Me | 4-Cl-Ph | NH-Ph | —CONH-cHex | trans | [70–72] |
| 1-103 | S | Me | Ph | —CONH-cHex | 4-CF$_3$O-Ph | trans | Oily substance |
| 1-104 | S | Me | Ph | | 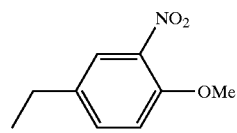 | —CONH-cHex | trans | |
| 1-105 | S | Me | 4-Me-Ph | —CONH-cHex | —CONH-cHex | trans | Oily substance*$^2$ |

TABLE 1-continued

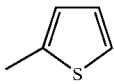

| Compound No. | X | $R_1$ | $R_2$ | $R_3$ | G | $R_1/R_2$ | Physical Constant [ ]:Melting Point ° C. |
|---|---|---|---|---|---|---|---|
| 1-106 | S | Me | 4-Me-Ph | —CONH-2-THP | —CONH-2-THP | trans | |
| 1-107 | S | Me | 4-Me-Ph | —CONH-(2-Me-cHex) | —CONH-(2-Me-cHex) | trans | |
| 1-108 | S | Me | 4-Me-Ph | H | —CONH-Ph | trans | [152.5–154] |
| 1-109 | S | Me | 4-Me-Ph | —COCH$_2$Cl | —CONH-cHex | trans | [155–157] |
| 1-110 | S | Me | 4-Me-Ph | H | —CONH-iPr | trans | [94–95] |
| 1-111 | S | Me | 4-Me-Ph | —CONH-cHex | —CONH-cHex | trans | [83–85] |
| 1-112 | S | Me | 4-Me-Ph | H | —CSNH-cHex | trans | [154–155] |
| 1-113 | S | Me | 4-Cl-Ph | H | CONHCO-2,6-diCl-Ph | trans | [220–223] |
| 1-114 | S | Me | 4-Cl-Ph | H | CONHCO-2,6-diCl-Ph | trans | [216–219] |
| 1-115 | S | Me | 4-Cl-Ph | H | —CONH-iPr | trans | [185] |
| 1-116 | S | Me | Ph | H | —CONHCOPh | trans | [168–169] |
| 1-117 | S | Me | Ph | H | —CONHCOPh | | |
| 1-118 | S | Me | Ph | —CONHCOPh | —CONHCOPh | trans | |
| 1-119 | S | Me | 2-thienyl (2-Me) | —CONH-cHex | —CONH-cHex | trans | |
| 1-120 | S | Me | 2-Naph | —CONH-cHex | —CONH-cHex | trans | |
| 1-121 | S | Me | 4-Me-Ph | —CONH-(3-Ac-cHex) | —Me | trans | |
| 1-122 | S | Me | 4-Me-Ph | —CONH-(3-OMe-2-THP) | —Ac | trans | |
| 1-123 | O | Me | 4-Me-Ph | —CONH-(3-OH-cHex) | —NO$_2$ | Cis | |

$^1$H NMR spectrum δ(CDCl$_3$):
*$^1$0.9~2.1 (m 13H), 3.45~3.9 (m 1H), 4.05~4.35 (m 1H), 4.4 (d 8 Hz 1H), 7.25~7.55 (m 5H)
*$^2$1.0~2.1 (m 23H), 2.2 (m 3H), 3.55~3.9 (m 2H), 4.0~4.05 (m 1H), 5.0~5.05 (d 1H), 5.05~5.2 (m 1H), 7.1 (m 4H), 9.7~9.8 (d 1H)

TABLE 2

| Compound No. | X | Y | Z | $R_1$ | $R_2$ | $R_4$ | $R_5$ | $R_1/R_2$ | Physical Constant [ ]:Melting Point ° C. |
|---|---|---|---|---|---|---|---|---|---|
| 2-1 | S | O | O | Me | 2-NO$_2$-Ph | H | cHex | trans | $n_D^{26}$ 1.5739 |
| 2-2 | S | O | S | Me | 4-Cl-Ph | Me | Me | trans | $n_D^{30}$ 1.6183 |
| 2-3 | S | O | O | Me | 4-MeS-Ph | H | cHex | trans | $n_D^{20}$ 1.5936 |
| 2-4 | S | O | O | Me | 4-CHF$_2$O-Ph | H | cHex | trans | [76–79] |
| 2-5 | S | O | O | Me | 4-AcO-Ph | H | cHex | trans | $n_D^{23.5}$ 1.5638 |
| 2-6 | S | O | O | Me | 4-Me-Ph | Et | cHex | trans | $n_D^{23.5}$ 1.5572 |
| 2-7 | S | O | O | Me | 4-Me-Ph | n-Pr | cHex | trans | $n_D^{20.5}$ 1.5551 |
| 2-8 | S | O | O | Me | 4-Cl-Ph | H | 4-CF$_3$O-Ph | trans | [136–138] |
| 2-9 | S | O | O | Me | 4-Cl-Ph | H | 2-F-4-Cl-6-iPrO-Ph | trans | [127–130] |
| 2-10 | S | O | O | Me | 4-Cl-Ph | H | O-Allyl | trans | $n_D^{21}$ 1.5501 |
| 2-11 | S | O | O | Me | 4-Cl-Ph | H | OEt | trans | [72–74] |
| 2-12 | S | O | O | Me | 4-Cl-Ph | H | 4-(2-Py)-Ph | trans | [158–160] |
| 2-13 | S | O | O | Me | 4-Ph-Ph | H | 2-THP | cis | [110–112] |
| 2-14 | S | O | O | Me | 4-Cl-Ph | H | 2,6-F$_2$-Bz | trans | [37–40] |
| 2-15 | S | O | O | Me | 4-Cl-Ph | H | 2-F-cHex | trans | [97–98] |
| 2-16 | S | O | O | Me | 4-Cl-Ph | H | 2-F-cHex | trans | [65–661] Diastereomer of No. 15 |
| 2-17 | S | O | O | Me | 4-Cl-Ph | H | 3,4-Br$_2$-cHex | trans | [66–67] |
| 2-18 | S | O | O | Me | 4-Cl-Ph | H | 2,3-Br$_2$-cHex | trans | [168–169] |
| 2-19 | S | O | O | Me | 4-nBu-Ph | H | 4-Cl-Ph | trans | [79–80] |

TABLE 2-continued

| No. | | | | | | | | | |
|---|---|---|---|---|---|---|---|---|---|
| 2-20 | S | O | O | Me | 4-nPn-Ph | H | 4-Cl-Ph | trans | [101–102] |
| 2-21 | S | O | O | Me | 4-Cl-Ph | H | 4-Py | trans | [167–169] |
| 2-22 | S | O | O | Me | 4-Cl-Ph | H | NMe$_2$ | trans | [91–92] |
| 2-23 | S | O | O | Me | 4-Cl-Ph | H | (4-F, 2-Cl, 5-Me-C$_6$H$_2$)-S-CH$_2$-C(=O)-OEt | trans | $n_D^{22.5}$ 1.6090 |
| 2-24 | S | O | O | Me | 4-FCH$_2$CH$_2$O-Ph | H | cHex | trans | $n_D^{26.5}$ 1.5445 |
| 2-25 | S | O | O | H | 3-Me-4-FCH$_2$CH$_2$O-Ph | H | 4-Morph | — | $n_D^{28}$ 1.5250 |
| 2-26 | S | O | O | Me | 4-Cl-Ph | H | CH(COOEt)CH$_2$CH$_2$COOEt | trans | $n_D^{19.5}$ 1.5219 |
| 2-27 | S | O | O | Me | 4-PhC$_2$H$_4$-Ph | H | 2-THP | trans | |
| 2-28 | S | O | O | Me | 4-Cl-Ph | Me | cHex | trans | [126–128] |
| 2-29 | S | O | O | Et | 4-Cl-Ph | H | cHex | trans | [78–79] |
| 2-30 | S | O | O | nPr | 4-Cl-Ph | H | cHex | trans | [109–110] |
| 2-31 | S | O | O | Me | 4-EtO-Ph | H | cHex | trans | $n_D^{24}$ 1.5527 |
| 2-32 | S | O | O | Me | 4-iPrO-Ph | H | cHex | trans | [73–75] |
| 2-33 | S | O | O | Me | 4-nPr-Ph | H | cHex | trans | $n_D^{27.5}$ 1.5458 |
| 2-34 | S | S | O | Me | 4-Cl-Ph | H | 2,4-Me$_2$-pyrimidin-6-yl (2,4,6-Me with N at 1,3) | trans | [151–153] |
| 2-35 | S | O | O | Me | 4-Cl-Ph | H | 2,4,6-Me$_3$-pyrimidinyl | trans | [175–177] |
| 2-36 | S | O | O | Me | 4-Cl-Ph | H | —SO$_2$-(2-Cl-Ph) | trans | [152-154] |
| 2-37 | S | S | O | Me | 4-Cl-Ph | H | —C$_2$H$_4$-4-Morph | trans | [123–126] |
| 2-38 | S | O | O | Me | 4-Cl-Ph | H | Bz | trans | $n_D^{22.5}$ 1.5973 |
| 2-39 | S | O | O | Me | 4-Cl-Ph | H | 2,6-Cl$_2$-Ph | trans | [106–107] |
| 2-40 | S | O | O | Me | 4-Cl-Ph | H | 2,6-Me$_2$-Ph | trans | [117–119] |
| 2-41 | S | O | O | Me | 4-CF$_3$-Ph | H | 2-THP | trans | |
| 2-42 | S | O | O | Me | 4-MeO-Ph | H | 2-THP | trans | |
| 2-43 | S | O | O | Me | 4-CF$_3$O-Ph | H | 2-THP | trans | |
| 2-44 | S | O | O | Me | 4-Cl-Ph | H | 2,3-(CF$_3$O)$_2$-cHex | trans | |
| 2-45 | S | O | O | Me | 4-CF$_3$-Ph | H | 3-MeO-cHex | trans | |
| 2-46 | O | O | O | Me | 4-Me-Ph | H | 4-Cl-Ph | trans | [142–144] |
| 2-47 | S | O | O | Me | 4-Me-Ph | H | 2-MeOCO-cHex | trans | |
| 2-48 | O | O | O | Me | 4-Me-Ph | H | C$_2$H$_4$Cl | trans | [78–80] |
| 2-49 | O | O | O | Me | 4-Me-Ph | H | Bn | trans | [89–91] |
| 2-50 | O | O | O | Me | 4-Me-Ph | H | —C$_2$H$_4$-Ph | trans | $n_D^{28}$ 1.5604 |
| 2-51 | O | O | O | Me | 4-Me-Ph | Me | cHex | trans | [97–99] |
| 2-52 | S | O | O | Me | 4-Me-Ph | H | 2-MeSO$_2$-cHex | trans | |
| 2-53 | O | O | O | Me | 4-Me-Ph | H | 2,6-Cl$_2$-Bz | trans | [147–149] |
| 2-54 | O | O | O | Me | 4-Me-Ph | H | CH(Me)COOEt | trans | $n_D^{22.5}$ 1.5208 |
| 2-55 | O | O | O | Me | 4-Me-Ph | H | SO$_2$NEt$_2$ | trans | $n_D^{16}$ 1.5340 |
| 2-56 | O | O | O | Me | 4-Me-Ph | H | SO$_2$OMe | trans | $n_D^{17}$ 1.5292 |
| 2-57 | O | S | O | Me | 4-Me-Ph | H | COOMe | trans | [89–92] |
| 2-58 | O | O | O | Me | 4-Me-Ph | Ac | cHex | trans | [107–110] |
| 2-59 | O | O | O | Me | 4-MeS-Ph | H | cHex | trans | [87.5–89] |
| 2-60 | O | O | O | Me | 4-Me-Ph | H | SO$_2$-(2-Me-Ph) | trans | [121–123] |
| 2-61 | O | O | O | Me | 3-CF$_3$-Ph | H | 2-THP | trans | $n_D^{30.5}$ 1.5012 |
| 2-62 | O | O | O | Me | 3-CF$_3$-Ph | H | 2-THP | trans | [104–106] Diastereomer of No. 61 |

TABLE 2-continued

| | | | | | | | | | |
|---|---|---|---|---|---|---|---|---|---|
| 2-63 | O | O | O | Me | 4-MeSO-Ph | H | cHex | trans | [112.5–116] |
| 2-64 | O | O | O | Me | 4-MeSO$_2$-Ph | H | cHex | trans | [172–175] |
| 2-65 | O | O | O | CH$_2$Cl | Ph | H | cHex | trans | $n_D^{22}$ 1.5519 |
| 2-66 | O | O | O | Me | 4-N(Me)$_2$-Ph | H | cHex | trans | [130–131.5] |
| 2-67 | O | O | O | CH$_2$Br | Ph | H | cHex | trans | $n_D^{17.5}$ 1.5624 |
| 2-68 | O | O | O | Me | 1-Naph | H | cHex | trans | [131–133] |
| 2-69 | O | O | O | Me | 1-Naph | H | 4-Cl-Ph | trans | [154–157] |
| 2-70 | O | O | O | Me | 2-Naph | H | cHex | trans | [99–101] |
| 2-71 | O | O | O | Me | 2-Naph | H | 4-Cl-Ph | trans | [180–182] |
| 2-72 | O | O | O | Me | 4-Me-Ph | H | 4-Cl-Ph | cis | [130–132] |
| 2-73 | O | O | O | Me | 4-Me-Ph | H | 2-Cl-Ph | cis | [165–167] |
| 2-74 | O | O | O | Me | 4-Ph-Ph | H | 2-Cl-Ph | cis | [123–125] |
| 2-75 | O | S | O | Me | 4-Ph-Ph | H | cHex | cis | [158–160] |
| 2-76 | O | O | O | H | Ph | H | 4-Cl-Ph | — | [168–171] |
| 2-77 | O | O | O | H | 4-Ph-Ph | H | 4-Cl-Ph | — | [205–208] |
| 2-78 | O | O | O | H | 4-Ph-Ph | H | 2-THP | — | [89–921] |
| 2-79 | O | O | O | Me | 4-Me-Ph | H | 2,6-F$_2$-Bz | cis | [134–136] |
| 2-80 | O | O | O | Me | 4-Ph-Ph | H | 2-THP | trans | [38–40] |
| 2-81 | O | O | O | CH$_2$F | Ph | H | cHex | trans | [94–96] |
| 2-82 | O | O | O | CH$_2$Cl | 4-Ph-Ph | H | 2-THP | trans | [54–57] |
| 2-83 | O | O | O | CH$_2$Cl | 4-Ph-Ph | H | cHex | trans | $n_D^{23}$ 1.5680 |
| 2-84 | O | O | O | Me | 4-tBu-Ph | H | 2-THP | cis | [148–150] |
| 2-85 | O | O | O | Me | 4-PhO-Ph | H | 2-THP | cis | [39–40] |
| 2-86 | O | O | O | Me | 4-(4-Cl-Ph)-Ph | H | 2-THP | cis | [165–167] |
| 2-87 | O | S | O | Me | 4-Ph-Ph | H | 2-THP | cis | [139–141] |
| 2-88 | O | O | O | Me | 4-cHex-Ph | H | 2-THP | trans | [176–177] |
| 2-89 | O | O | O | Me | 4-(4-Cl-Ph)-Ph | H | 4-Cl-Ph | cis | [222–223] |
| 2-90 | O | O | O | Me | 4-(4-Me-Ph)-Ph | H | 4-Cl-Ph | cis | [219–222] |
| 2-91 | O | O | O | Me | 4-Ph-Ph | H | ![tetrahydrothiopyran] | cis | [167–168] |
| 2-92 | O | O | O | Me | 4-nBu-Ph | H | 4-Cl-Ph | cis | [168–170] |
| 2-93 | O | O | O | Me | 4-cHex-Ph | H | 4-Cl-Ph | trans | [136–138] |
| 2-94 | O | O | O | Me | 4-nPn-Ph | H | 4-Cl-Ph | cis | [147–149] |
| 2-95 | O | O | O | Me | 4-(4-Me-Ph)-Ph | H | 2-THP | cis | [150–153] |
| 2-96 | O | O | O | Me | 3-Ph-Ph | H | 4-Cl-Ph | cis | [149–151] |
| 2-97 | O | O | O | Me | 4-Ph-Ph | H | 4-Py | cis | [186] |
| 2-98 | O | O | O | Me | 4-Ph-Ph | H | 4-Morph | cis | [164–165] |
| 2-99 | O | O | O | Me | 4-Ph-Ph | H | NMe$_2$ | trans | [135–137] |
| 2-100 | O | O | O | Me | 3-Ph-Ph | H | 2-THP | cis | [55–58] |
| 2-101 | O | O | Me | 4-nBu-Ph | H | 2-THP | | cis | [77–80] |
| 2-102 | O | O | O | Me | 4-(2-Py)-Ph | H | 4-Cl-Ph | cis | [214–216] |
| 2-103 | O | O | O | Me | 4-Me-Ph | H | NMe$_2$ | trans | [115–116] |
| 2-104 | O | O | O | Me | 2,6-Cl$_2$-Ph | H | 4-Cl-Ph | trans | [146–147] |
| 2-105 | O | O | O | Me | 4-Ph-Ph | H | 1-Pip | cis | [150–151] |
| 2-106 | O | O | O | Me | 4-(4-Cl-Ph)-Ph | H | 1-Pip | trans | [180–182] |
| 2-107 | O | O | O | Me | 4-(4-Cl-Ph)-Ph | H | 1-Pip | cis | [196–198] |
| 2-108 | O | O | O | Me | 4-Me-Ph | H | —NH-Ph | trans | [129–132] |
| 2-109 | O | O | O | Me | 4-(4-CF$_3$-Ph)-Ph | H | 2-THP | cis | |
| 2-110 | O | O | O | Me | 2,6-diF-Ph | H | 2,4-diCl-Ph | cis | [135–137] |
| 2-111 | O | O | O | Me | 4-Me-Ph | H | —CH(—COOEt)—C$_2$H$_4$COOEt | cis | $n_D^{19.5}$ 1.5068 |
| 2-112 | O | O | O | Me | 4-Me-Ph | H | —C$_2$H$_4$NEt$_2$ | cis | $n_D^{20.5}$ 1.5209 |
| 2-113 | O | O | O | Me | 1-Naph | H | 2-THP | cis | [74–80] |
| 2-114 | O | O | O | Me | 4-Ph-Ph | Me | 2-THP | cis | $n_D^{18}$ 1.5603 |
| 2-115 | O | O | O | Me | 2-Naph | H | 2-THP | cis | Oil |
| 2-116 | O | O | O | Me | 4-PhO-Ph | H | —OEt | cis | [119–120] |
| 2-117 | O | O | O | Me | 4-Bn-Ph | H | 2-THP | cis | [103–107] |
| 2-118 | O | O | O | Me | 4-PhO-Ph | H | —C$_2$H$_4$OC$_2$H$_4$OEt | cis | $n_D^{20}$ 1.5330 |
| 2-119 | O | O | O | Me | 4-PhS-Ph | H | 2-THP | cis | [108–114] |
| 2-120 | O | O | O | Me | 4-PhO-Ph | H | —CH$_2$-2-THF | cis | $n_D^{20}$ 1.5640 |
| 2-121 | O | O | O | Me | 4-Ph-Ph | H | Me | cis | [118–123] |
| 2-122 | O | O | O | Me | 2-(1-MeO)-Naph | H | 2-THP | cis | [158–162] |
| 2-123 | O | O | O | Me | 4-PhO-Ph | H | 2-Dxn | cis | $n_D^{19}$ 1.5507 |
| 2-124 | O | O | O | Me | 2-Naph | H | 2-Dxn | cis | $n_D^{20}$ 1.5605 |
| 2-125 | O | O | O | Me | ![methyl-tetrahydronaphthalene] | H | 2-THP | cis | [60–62] |
| 2-126 | O | O | O | Me | 2-Naph | H | SO$_2$N(Et)–iPr | cis | $n_D^{25}$ 1.5544 |

TABLE 2-continued

| No. | | | | | Ar | | R | | Note |
|---|---|---|---|---|---|---|---|---|---|
| 2-127 | O | O | O | Me | 5-methyl-indanyl | H | 2-THP | cis | [52–56] |
| 2-128 | O | O | O | Me | 4-PhO-Ph | H | 2-THF | cis | [103–106] |
| 2-129 | O | O | O | Me | 2-Naph | H | 2-THF | cis | Oily substance |
| 2-130 | O | O | O | H | 2-Naph | H | 2-THP | — | [117–120] |
| 2-131 | O | O | O | H | 2-Naph | H | 2-THP | — | Oily substance |
| 2-132 | O | O | O | Me | 2-Naph | H | —C(=O)nBu | cis | [84–87] |
| 2-133 | O | O | O | Me | 2-Naph | H | 2-(6-MeO–THP) | cis | $n_D^{27}$ 1.5655 |
| 2-134 | O | O | O | Me | 2-Naph | H | 2-Dxln | cis | [116–124] |
| 2-135 | O | O | O | Me | 6-methyl-tetrahydronaphthyl | H | 2-(6-MeO-THP) | cis | $n_D^{31}$ 1.5462 |
| 2-136 | O | O | O | Me | 6-methyl-7-methoxy-naphthyl | H | 2-THP | cis | Oily substance |
| 2-137 | O | O | O | Me | 4-(2-thienyl)-Ph | H | 2-THP | trans | |
| 2-138 | O | O | O | Me | 4-Ph-Ph | H | 3-MeO-cHex | cis | |
| 2-139 | O | O | O | Me | 4-Ph-Ph | H | 4-oxo-cHex | cis | |
| 2-140 | O | O | O | Me | 4-Ph-Ph | H | 4-MeO-Ph | cis | |
| 2-141 | O | O | O | Me | 4-Ph-Ph | H | 4-NO$_2$-Ph | cis | |
| 2-142 | O | O | O | Me | 4-Ph-Ph | H | 4-MeSO$_2$-Ph | cis | |
| 2-143 | O | O | O | Me | 2-thienyl | H | 4-CF$_3$-Ph | trans | $n_D^{18}$ 1.5506 |
| 2-144 | O | O | O | Me | 2-thienyl | H | 4-Cl-Ph | trans | [132 –133] |
| 2-145 | S | O | O | Me | 3-Py | H | cHex | trans | [88–90] |
| 2-146 | O | O | O | Me | 2-Py | H | 4-Cl-Ph | cis | $n_D^{28}$ 1.6070 |
| 2-147 | O | O | O | Me | 3-tetrahydrothiopyranyl | H | 4-Cl-Ph | | [180–200] |
| 2-148 | O | O | O | Me | 3-tetrahydrothiopyranyl | H | 4-Cl-Ph | | $n_D^{22}$ 1.5815 |
| 2-149 | O | O | O | Me | 5-(3,6-dihydro-2H-thiopyranyl) | H | 4-Cl-Ph | trans | [110–111] |
| 2-150 | O | O | O | Me | 5-(3,6-dihydro-2H-thiopyranyl) | H | 4-Cl-Ph | cis | [185–187] |

TABLE 2-continued

| | | | | | | | | | |
|---|---|---|---|---|---|---|---|---|---|
| 2-151 | O | O | O | Me | 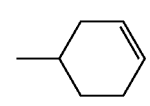 | H | 2-THP | cis | [166–169] |
| 2-152 | O | O | O | Me | 3,4-(MeO)$_2$-Ph | H | cHex | trans | [127–128.5] |
| 2-153 | O | O | O | Me | 3,4-OCH$_2$O-Ph | H | 2-THP | trans | [127–129] |
| 2-154 | O | O | O | Me | 4-Me-Ph | H | 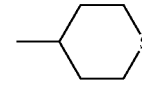 | trans | [95–96] |
| 2-155 | O | O | O | Me | Ph | H | 2-THP | trans | $n_D^{19.3}$ 1.5395 |
| 2-156 | O | O | O | Me | 3,4-diMe-Ph | H | 2-THP | trans | [88–90] |
| 2-157 | O | O | O | Me | 4-Me-Ph | H | 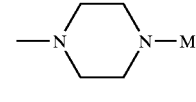 | trans | [109–111] |
| 2-158 | O | O | O | Me | 4-Cl-Ph | H | 2-THP | trans | [75–76] |
| 2-159 | O | O | O | Me | 4-Me-Ph | H | 4-THP | trans | [95–97] |
| 2-160 | O | O | O | Me | 4-Me-Ph | H | 2-Dxn | trans | [85–104] |
| 2-161 | O | O | O | Me | 4-Me-Ph | H | 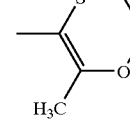 | trans | [78–80] |
| 2-162 | O | O | O | Me | 4-Me-Ph | H | 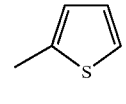 | trans | $n_D^{20.5}$ 1.5603 |
| 2-163 | O | O | O | Me | 4-F-Ph | H | cHex | trans | [122–123] |
| 2-164 | O | O | O | Me | 3-CF$_3$-Ph | H | cHex | trans | [125–127] |
| 2-165 | O | O | O | Me | 3-Cl-Ph | H | cHex | trans | [105–107] |
| 2-166 | O | O | O | Me | 2,4-Cl$_2$-Ph | H | cHex | trans | [80–82] |
| 2-167 | O | O | O | Me | 4-MeO-Ph | H | cHex | trans | [76–78] |
| 2-168 | O | O | O | Me | 3,4-Me$_2$-Ph | H | cHex | trans | [66–68] |
| 2-169 | O | O | O | Me | 4-Br-Ph | H | cHex | trans | [126–128] |
| 2-170 | O | O | O | Me | 4-Me-Ph | H | 2-THP | trans | [94.5–94.6] |
| 2-171 | O | O | O | Me | 4-tBu-Ph | H | cHex | trans | [105–107] |
| 2-172 | O | O | O | Me | 3,4-Cl-Ph | H | cHex | trans | [160–162] |
| 2-173 | O | O | O | Me | 4-CF$_3$-Ph | H | cHex | trans | [152–154] |
| 2-174 | O | O | O | Me | 3,4-OCH$_2$O-Ph | H | cHex | trans | [74–76] |
| 2-175 | O | O | O | Me | 4-ipr-Ph | H | cHex | trans | [76–78] |
| 2-176 | O | O | O | Me |  | H | cHex | trans | [45–47] |
| 2-177 | O | O | O | Me | 4-nC$_{12}$H$_{25}$-Ph | H | cHex | trans | [50–52] |
| 2-178 | O | O | O | Me | 3-Cl-Ph | H | cHex | trans | [89–90.5] |
| 2-179 | O | O | S | Me | 4-Me-Ph | H | 2-THP | trans | $n_D^{20.5}$ 1.5800 |
| 2-180 | O | S | O | Me | Ph | H | cHex | trans | [93–95] |
| 2-181 | O | O | S | Me | 4-Cl-Ph | H | cHex | trans | [89–91] |
| 2-182 | O | S | O | Me | 3,4-diMe-Ph | H | cHex | trans | [90–92] |
| 2-183 | O | O | O | Me | 4-PhO-Ph | H | 4-Cl-Ph | trans | [164–165] |
| 2-184 | O | O | O | Me | 3-Ph-Ph | H | cHex | trans | [112–115] |
| 2-185 | O | O | O | Me | 4-Ph-Ph | H | cHex | trans | [134–136] |
| 2-186 | O | O | O | Me | 4-Ph-Ph | H | 4-Cl-Ph | trans | [137–139] |
| 2-187 | O | O | O | Me | 4-Ph-Ph | H | 4-Cl-Ph | cis | [216–218] |
| 2-188 | O | O | O | Me | 3-PhO-Ph | H | cHex | trans | [98–101] |
| 2-189 | S | O | O | Me | 4-Me-Ph | H | 2-THP | trans | $n_D^{27}$ 1.5638 |
| 2-190 | S | O | O | Me | 4-nC$_{12}$H$_{25}$-Ph | H | cHex | trans | [46–49] |
| 2-191 | S | S | O | Me | 4-Me-Ph | H | cHex | trans | [94.5–97] |
| 2-192 | S | O | O | Me | 2-Me-Ph | H | cHex | trans | [116–117.5] |
| 2-193 | O | O | O | Me | 3,4-Cl$_2$-Ph | H | cHex | trans | [136–138] |
| 2-194 | S | S | O | Me | 4-Cl-Ph | H | cHex | trans | [108–110] |
| 2-195 | S | O | O | Me | 4-MeO-Ph | H | cHex | trans | $n_D^{30.5}$ 1.5590 |
| 2-196 | S | O | O | Me | 2-Cl-Ph | H | cHex | trans | [97–99] |
| 2-197 | S | O | O | Me | 3-Me-Ph | H | cHex | trans | $n_D^{30}$ 1.5657 |
| 2-198 | S | O | O | Me | 3,5-Me$_2$-Ph | H | cHex | trans | [99–102.5] |

TABLE 2-continued

| Compound No. | X | Y | Z | R1 | R2 | R4 | R5 | R1/R2 | Physical Constant [ ]:Melting Point ° C. | Optical Rotation (CHCl3) |
|---|---|---|---|---|---|---|---|---|---|---|
| 2-199 | S | O | O | Me | 4-Et-Ph | H | cHex | trans | [85.5–88] | |
| 2-200 | S | O | O | Me | 4-Cl-Ph | H | 2-THP | trans | $n_D^{29}$ 1.5801 | |
| 2-201 | S | O | O | Me | 4-Cl-Ph | H | 2-THP | trans | $n_D^{29}$ 1.5760 | |
| 2-202 | S | O | O | Me | 4-CH$_2$Br-Ph | H | cHex | trans | [106–108] | |
| 2-203 | S | O | O | Me | 3-Cl-4-Me-Ph | H | cHex | trans | [120–121] | |
| 2-204 | S | O | O | Me | 2,4-Me$_2$-Ph | H | cHex | trans | [95–97] | |
| 2-205 | S | O | O | Me | 4-iPr-Ph | H | cHex | trans | [120–123] | |
| 2-206 | S | O | O | Me | 4-Me-Ph | H | 2-DXn | trans | $n_D^{27.5}$ 1.5679 | |
| 2-207 | S | O | O | Me | 4-Me-Ph | H | (4-cyclohexenyl) | trans | [67–68] | |
| 2-208 | S | O | O | Me | 2-Thienil | H | cHex | trans | [133–134] | |
| 2-209 | S | O | O | Me | 3,4-(MeO)$_2$-Ph | H | cHex | trans | [117–119] | |
| 2-210 | S | O | O | Me | 4-NO$_2$-Ph | H | cHex | trans | [144–147] | |
| 2-211 | S | O | O | Me | 4-Me-Ph | H | 2-OH-cHex | trans | | |
| 2-212 | S | O | O | Me | 4-Me-Ph | H | 3-OH-cHex | trans | | |
| 2-213 | S | O | O | Me | 4-Me-Ph | H | 3-oxo-cHex | trans | | |
| 2-214 | S | O | O | Me | 4-Me-Ph | H | 4-OH-cHex | trans | | |
| 2-215 | S | O | O | Me | 4-Me-Ph | H | 2-oxo-cHex | trans | | |
| 2-216 | S | O | O | Me | 4-Me-Ph | H | 4-oxo-cHex | trans | | |
| 2-217 | S | O | O | Me | 4-Me-Ph | H | 3,4-(OH)$_2$-cHex | trans | | |
| 2-218 | S | O | S | Me | 3-CF$_3$-Ph | H | cHex | trans | $n_D^{21.5}$ 1.5775 | |
| 2-219 | S | O | O | Me | 4-Ph-Ph | H | cHex | trans | [145–147] | |
| 2-220 | O | O | O | Me | 4-Me-Ph | H | 4-Morph | trans | [124–125] | |
| 2-221 | O | O | O | Me | Ph | H | 4-Morph | trans | [110–111] | |
| 2-222 | O | O | O | Me | 4-Me-Ph | H | 1-Pip | trans | [96–98] | |
| 2-223 | O | O | O | Me | 4-Me-Ph | H | 1-Pyld | trans | [81–83] | |
| 2-224 | O | O | O | Me | 4-Me-Ph | H | (4-Me-piperazin-1-yl) | trans | [98–100] | |
| 2-225 | O | O | O | Me | 4-Me-Ph | H | 4-(2,6-diMe-Morph) | trans | [64–65] | |
| 2-226 | O | O | O | Me | 4-CF$_3$-Ph | H | 1-Pip | trans | [131–132] | |
| 2-227 | O | O | O | Me | 3,4-OCH$_2$O-Ph | H | 1-Pip | trans | [90–91] | |
| 2-228 | O | O | O | Me | 3,4-Me$_2$-Ph | H | 4-Morph | trans | [116–117] | |
| 2-229 | S | O | O | Me | 4-F-Ph | H | 4-Morph | trans | [144–146] | |
| 2-230 | S | O | O | Me | 4-Me-Ph | H | 4-Morph | trans | [115–116] | |
| 2-231 | S | O | O | Me | Ph | H | 4-Morph | trans | [121–122] | |
| 2-232 | S | O | O | Me | 4-Me-Ph | H | 1-Pip | trans | [107–108] | |
| 2-233 | S | O | O | Me | Ph | H | 1-Pip | trans | [123–124] | |
| 2-234 | S | O | O | Me | 4-Cl-Ph | H | 1-(2,6-diMe-Pip) | trans | $n_D^{24}$ 1.5420 | |
| 2-235 | S | O | O | Me | 3-CF$_3$-Ph | H | 1-Pip | trans | [117–118] | |
| 2-236 | S | O | O | Me | 4-MeO-Ph | H | 4-Morph | trans | [119–120] | |
| 2-237 | S | O | S | Me | 4-Me-Ph | H | 4-Morph | trans | [101–103] | |
| 2-238 | S | O | O | Me | 4-CN-Ph | H | 2-THP | trans | | |
| 2-239 | S | O | O | Me | 4-COOMe-Ph | H | 2-THP | trans | | |
| 2-240 | S | O | O | Me | 4-COOCF$_3$-Ph | H | 2-THP | trans | | |
| 2-241 | O | O | O | Me | 4-CONH$_2$-Ph | H | 2-THP | cis | | |
| 2-242 | O | O | O | Me | 4-CONHMe-Ph | H | 2-THP | cis | | |
| 2-243 | S | O | O | Me | 4-Me-Ph | H | 6-OXO-2-THP | trans | | |
| 2-244 | O | O | O | Me | 4-Me-Ph | H | 2-THP | trans (4R, 5R) | [88–91] | $[\alpha]_D^{23}$ + 6.2° |
| 2-245 | O | O | O | Me | 4-Me-Ph | H | 2-THP | trans (4R, 5R) | [121–125] | $[\alpha]_D^{23}$ +]19.2° Diastereomer |
| 2-246 | S | O | O | Me | 4-Cl-Ph | H | 2-THP | trans (4R, 5R) | $n_D^{31.5}$ 1.5789 | $[\alpha]_D^{25}$ + 176° |
| 2-247 | S | O | O | Me | 4-Cl-Ph | H | 2-THP | trans (4R, 5R) | [120–122] | $[\alpha]_D^{25}$ + 199.8° Diastereomer |

PHARMACOLOGICAL TEST EXAMPLE 1

PLA(2) Activity

The PLA(2) activity was measured by quantitatively analyzing the fluorescent product of hydrolysis from 1,2-bis-(4,4-difluoro-5,7-dimethyl-4-bora-3a,4a-diaza-s-indecene-3-undecanoyl)-sn-glycero-3-phosphocholine (hereinafter referred to bis-BODIPY®FL C$_{11}$—PC, Molecular Probes, Inc., B-7701) using activated U937 cells (human monoblastic lymphoma cell line) by inflammatory stimulus (Meshulam, T. et al., *The journal of Biological Chemistry* 267 (30): 21465–21470 (1992); and Solito, E. et al., *British Journal of Pharmacology* 124: 1675–1683 (1998).). The substrate bis-BODIPY®FL C$_{11}$—PC is incorporated into cellular membranes, the proximity of the BODIPY FL fluorophores on adjacent phospholipid acyl chains causes fluorescence self-quenching. Separation of the fluorophores upon hydrolytic cleavage of one of the acyl chains by PLA(1) or the PLA(2) results in increased fluorescence. In the activated U937 by inflammatory stimulus, it is shown that this substrate should be cleaved enzymatically by IV-cPLA(2) from the feature of its behaviors including sensitivity profiles against the inhibitors.

The human cell line U937 was purchased from Dai-Nippon Pharmaceuticals Co., Ltd. The cells were maintained by transferring every 3–4 days into RPMI 1640 medium (Sigma Chemical Co., R6504) supplemented with heat-inactivated 10% fetal bovine serum (Fetal Bovine Serum, Sigma Chemical Co., F 4135) in a 5% $CO_2$ humidified atmosphere at 37° C. The cells were transferred into the culture medium described above, containing 1.2% (v/v) dimethylsulfoxide (hereinafter referred to as DMDO, Nacalai tesque Co., Ltd., D 134-45), and pre-cultured for 96 to 120 hours so as to differentiate into the macrophage-like cells to be provided for the assay. The macrophage-like cells were collected and washed by centrifugation with the Assay medium (Dulbecco's phosphate buffered saline (hereinafter referred to as PBS)-2.2 mM glucose-2.5 µm albumin). Then, Phorbol 12-Myristate 13-Acetate (hereinafter referred to as TPA, Sigma Chemical Co., P 8139) was added to the Assay medium to be $1\times10^{-8}$M as the final concentration. Then, the macrophage-like cells were further cultured for an hour to be activated (Rzigalinski, B. A. & Rosenthal, M. D., *Biochimica et Biophysica Acta* 1223: 219–225 (1994); and Gonchar, M. V. et al., *Biochemical and Biophysical Research Communication*, 249: 829–832 (1998).).

For preparing substrate liposome suspension, bis-BODIPY®FL $C_{11}$—PC was combined with phosphatidylcholine (Sigma Chemical Co., P 7769) at 1:9 molar ratio in chloroform, and dried under nitrogen flow. The dried mixture was suspended with the Assay medium at 100 µg/mL, voltexed and sonicated for an hour on ice under dark condition.

The test compound was dissolved with DMSO at 30 mM, and the solution diluted with either DMSO or the Assay medium before addition into the reaction mixture. The DMSO concentration in the reaction mixture was controlled so as to be no more than 0.1%. The 30-fold concentration of test compound solution was put into each well of MICRPTEST™ Tissue Culture Plate, 96 Well (Falcon, 3072) at a rate of 2.5 µL/well. To the respective well was added 25 µL/well of the activated U937 cell suspension ($6\times10^{-6}$ cells/mL), and the cells were pre-cultured for 120 min. at 37° C. in a 5% $CO_2$ atmosphere incubator. 47.5 µL/well of the substrate liposome suspension with $1.5\times10^{-6}$M A23187 (Sigma Chemical Co., C 7522) was added into each well to prepare 75 µL/well of the total reaction mixture, followed by culture for 30 min. under the same conditions with shielding against light. 100 µL/well of 0.1% GEDTA (Dojindo Laboratories Co. Ltd., 348-01311) methanol solution was added into each well and mixed to stop the reaction. The increased fluorescence of the hydrolysis product by the enzyme was determined by measuring the fluorescence emission intensity at 535 nm with excitation at 485 nm from the top side of each plate at 37° C., using a Multi Functional Microplate Reader SPECTRA FLUOR PLUS (TECAN Austria GmbH). The measurements for the same test lot were carried out under the same sensitivity as the optimum gain condition for the first microplate measurement. In the test, each treatment was repeated three times, the reaction mixture plot without cells was used as the blank, and arachidonyl trifluoromethyl ketone (hereinafter referred to as $AACOCF_3$, Calbiochem-Novabiochem Corp., 100109) was used for the positive control treatment. PLA(2) activity in each test plot was determined by subtracting the mean value of the fluorescence emission intensity in the blank plot from that of each well, respectively. There was statistically no significant difference between the plots with and without 0.1% DMSO. In the pre-examination, the fluorescence emission intensity based on the substrate hydrolysis was increased linearly with time progression until 90 min. Besides, hydrolysis as the basic metabolic activity, which was measured as the enzymatic activity in the subcultured cells neither being differentiated nor activated, without A23187 treatment condition, was shown about one seventh of that exerted by the activated cells. Thus, the difference obtained by subtracting the basic metabolic activity from each enzymatic activity was determined as the inflammatory activated PLA(2) activity, and the inhibition rate was calculated by the inflammatory activated PLA(2) activity per the mean value of that of the control plots with and without DMSO, for evaluating the activity of the respective test compounds. The inhibitory activity measured for the respective compounds of the present invention are shown in Table 3 below, for example.

TABLE 3

| Compound No. | Concentration (µM) | Inhibition (%) |
| --- | --- | --- |
| 1-1 | 0.1 | 97 |
| 1-5 | 0.1 | 66 |
| 1-10 | 0.1 | 79 |
| 1-11 | 0.1 | 88 |
| 1-12 | 0.1 | 52 |
| 1-22 | 0.1 | 84 |
| 1-25 | 0.1 | 100 |
| 1-28 | 0.1 | 93 |
| 1-35 | 0.1 | 57 |
| 1-49 | 0.1 | 91 |
| 1-42 | 0.1 | 94 |
| 1-73 | 0.1 | 68 |
| 1-77 | 1 | 100 |
| 1-112 | 1 | 72 |
| 2-21 | 1 | 100 |
| 2-22 | 0.1 | 100 |
| 2-26 | 0.1 | 77 |
| 2-36 | 0.1 | 61 |
| 2-37 | 0.1 | 63 |
| 2-38 | 1 | 87 |
| 2-48 | 0.1 | 77 |
| 2-54 | 0.1 | 95 |
| 2-55 | 0.1 | 94 |
| 2-56 | 0.1 | 92 |
| 2-60 | 0.1 | 100 |
| 2-75 | 0.1 | 83 |
| 2-78 | 0.01 | 100 |
| 2-79 | 0.1 | 55 |
| 2-113 | 1 | 72 |
| 2-115 | 0.1 | 63 |
| 2-116 | 0.1 | 54 |
| 2-117 | 0.1 | 82 |
| 2-125 | 0.1 | 62 |
| 2-126 | 0.1 | 72 |
| 2-127 | 0.01 | 54 |
| 2-128 | 1 | 81 |
| 2-130 | 0.1 | 68 |
| 2-133 | 1 | 75 |
| 2-135 | 0.01 | 64 |
| 2-145 | 0.1 | 72 |
| 2-146 | 0.1 | 85 |
| 2-151 | 0.01 | 64 |
| 2-155 | 0.1 | 95 |
| 2-156 | 0.1 | 88 |
| 2-157 | 0.1 | 96 |
| 2-159 | 0.1 | 95 |
| 2-161 | 1 | 65 |

TABLE 3-continued

| Compound No. | Concentration (μM) | Inhibition (%) |
|---|---|---|
| 2-170 | 0.1 | 82 |
| 2-176 | 0.1 | 100 |
| 2-180 | 0.1 | 100 |
| 2-182 | 0.1 | 91 |
| 2-186 | 0.1 | 75 |
| 2-187 | 0.1 | 74 |
| 2-189 | 0.01 | 86 |
| 2-194 | 1 | 78 |
| 2-201 | 1 | 94 |
| 2-244 | 0.1 | 78 |
| 2-245 | 0.1 | 93 |
| 2-246 | 0.01 | 78 |
| AACOCF$_3$ | 3 | 65 |

PHARMACOLOGICAL TEST EXAMPLE 2

Mouse Ear Edema Induced by TPA

This test was carried out referring to the method of Carlson, R. P. et al. (*Agents and Actions*, 17(2): 197–204 (1985).) and the method of Chang, J. (*European Journal of Pharmacology*, 142: 197–205 (1987).). More specifically, 5 μg/20 μL of TPA (Sigma Chemical Co.), dissolved with ethanol, was topically applied to the anterior and posterior surfaces of the right ear of an ICR-strain male mouse (6–7 weeks old). 6 hours later, the thickness of each ear at the particular part was respectively measured three times using a digimatic micrometer to calculate the mean value. Ear edema was determined by subtracting the mean thickness of the left ear as without treatment from that of the right ear as TPA-applied. Topical application activity was evaluated by applying an acetone solution of the compound of the present invention or 0.1% Tween 80/acetone solution thereof similarly to the anterior and posterior surfaces of the right ear 30 min. before and 15 min. after the TPA-application. As the positive control, an acetone solution of Dexamathasone-21-acetate (hereinafter referred to as DEX-Ac, Sigma Chemical Co., D 1881) and an acetone solution of indomethacin were applied similarly as for the compound of the present invention. Oral administration activity was evaluated by administrating 0.2% Tween 80 suspension of the compound of the present invention forcibly and perorally to the mouse an hour prior to the TPA-application. As the positive control, 100 mg/kg of Hydrocortisone (Sigma Chemical Co., H 4001) suspension was applied to the mouse similarly as for the compound of the present invention. By the treatment with the compounds of the present invention, anti-inflammatory activities, for example as shown in Table 4, were measured for the respective compounds. Furthermore, it was noted that the mice of both DEX-Ac administration group and indomethacin administration group showed generally bad symptoms and reducing their body weight after 24 hours. On the contrary, the mice in the each group applied with the compounds of the present invention showed good condition and no significant change in their body weight.

TABLE 4

| Compound No. | Dose (mg/μL/ear × 2) | Ear Edema Inhibition (%) |
|---|---|---|
| 1-12 | 0.3 mg/20 μL/ear × 2 | 79 |
| 1-22 | 0.3 mg/20 μL/ear × 2 | 56 |
| 1-28 | 1 mg/20 μL/ear × 2 | 36 |
| 1-73 | 1 mg/40 μL/ear × 2 | 86 |
| 1-90 | 1 mg/20 μL/ear × 2 | 41 |
| 1-112 | 1 mg/40 μL/ear × 2 | 69 |
| 2-26 | 0.3 mg/20 μL/ear × 2 | 86 |
| 2-36 | 0.3 mg/20 μL/ear × 2 | 41 |
| 2-54 | 0.3 mg/20 μL/ear × 2 | 64 |
| 2-55 | 1 mg/40 μL/ear × 2 | 54 |
| 2-60 | 1 mg/20 μL/ear × 2 | 53 |
| 2-125 | 1 mg/40 μL/ear × 2 | 62 |
| 2-127 | 1 mg/40 μL/ear × 2 | 81 |
| 2-128 | 1 mg/40 μL/ear × 2 | 49 |
| 2-135 | 0.3 mg/20 μL/ear × 2 | 84 |
| 2-146 | 1 mg/40 μL/ear × 2 | 80 |
| 2-156 | 1 mg/20 μL/ear × 2 | 48 |
| 2-170 | 0.3 mg/20 μL/ear × 2 | 57 |
| 2-189 | 0.3 mg/20 μL/ear × 2 | 84 |
| 2-244 | 1 mg/40 μL/ear × 2 | 48 |
| 20246 | 1 mg/40 μL/ear × 2 | 74 |
| DEX-Ac | 1 mg/20 μL/ear × 2 | 80 |
| DEX-Ac | 0.3 mg/20 μL/ear × 2 | 49 |

PHARMACOLOGICAL TEST EXAMPLE 3

Mouse Delayed Contact Dermatitis Induced by Picryl Chloride

This pharmacological test was carried out referring to the method of Asherson, G. L. & Ptak, W. (*Immunology*, 15: 405–416 (1968).) and the method of Jun Hiroi (*Folia Pharmacology of Japan*, 86: 233–239 (1985).). More specifically, hairs on the abdomen of an ICR-strain male mouse were removed using an electric clip and an electric shaver. Then, 0.1 mL of 7% ether solution of picryl chloride (Tokyo Kasei Kogyo Co., Ltd., C 0307) was applied onto the abdomen for sensitization. On the sixth day after the sensitization, 20 μL/ear of 1% olive oil solution of picryl chloride was topically applied to the anterior and posterior surfaces of both ears of the mouse to induce contact dermatitis (first induction). Before and 24 hours after the induction, the thicknesses of the particular parts on the both ears were measured three times, respectively, using a digimatic micrometer (Mitsutoyo Co., Ltd.) to work out the average values. Ear edema of the both ears was respectively determined by subtracting the average thickness of the each ear before the induction from that on 24 hours after the induction, so that a grouping was carried out to separate the appropriate individuals. On the fourth day after the first induction, the hairs on the abdomen were removed again, and 0.1 mL of 7% ethanol solution of picryl chloride was applied thereto for additional sensitization. The contact dermatitis for evaluating activity was induced by re-applying 20 μL/ear of 1% olive oil solution of picryl chloride to the anterior and posterior surfaces of both ears (second induction) on the seventh day after the additional sensitization (on the 18th day after the first sensitization). The activity of each compound of the present invention was evaluated as the inhibition on the contact dermatitis as compared with that of the vehicle applied control. That is, the thicknesses of the particular portions of the both ears were measured respectively three times with a digimatic micrometer to work out the mean values before, 24 hours and 48 hours after the second induction. Ear swelling was determined by subtracting the ear thickness before the second induction from that on 24 hours and 48 hours after the second induction, respectively. Topical application activity was evaluated by applying 25 μL of the acetone solution of the compound of the present invention similarly to the anterior and posterior surfaces of the right ear one hour before and 16 hours after the second induction. As the positive control, 0.02 mg/20 µL of acetone solution of Dexamethasone (hereinafter referred to as DEX, Wako Pure Chemical Industries Ltd., 047-18863) was applied similarly as for the compound of the present invention. With respect to the inhibitory activity in topical application tests, the topical activity was determined by the inhibition of the applied right ear edema, and the translocation and distribution property was determined by the activity onto the swelling of non-treated left ear. Oral administration activity was evaluated by administrating 0.5% methyl cellulose suspension of the compound of the present invention forcibly and perorally to the mouse an hour before and 16 hours after the second induction. As the positive control, 20 mg/kg of Prednisolone (Sigma Chemical Co., P 6004) suspension was administered similarly as for the compounds of the present invention. With respect to the compounds of the present invention, the anti-allergic activities as shown in Table 4 were measured. Furthermore, it was noted that the mice of DEX administered group showed generally bad symptoms and reducing their body weight significantly 48 hours after the second induction. On the contrary, the mice in the each group applied with the compounds of the present invention showed good condition and no significant change in their body weight. As the examples, the body weight changes in the mice for 48 hours after the second induction when they were administrated with the compounds shown in Table 5 are shown in Table 6.

TABLE 5

| Compound No. | Dose (mg/25 µL/ ear × 2) | Ear swelling after 24 hours | |
|---|---|---|---|
| | | Right (Applied) (Mean ± S.E., mm) | Left (Not applied) (Mean ± S.E., mm) |
| Vehicle Control | — | 0.288 ± 0.012 | 0.273 ± 0.013 |
| 1-43 | 1.5 | 0.196 ± 0.029 | 0.201 ± 0.008 |
| 2-194 | 1.5 | 0.223 ± 0.010 | 0.226 ± 0.016 |
| 2-240 | 1.5 | 0.246 ± 0.009 | 0.238 ± 0.024 |
| DEX | 0.02 | 0.057 ± 0.009 | −0.005 ± 0.033 |

TABLE 6

| Compound No. | Dose (mg/ear × 2) | Body weight before induction (Mean ± S.E.) (g) | Change in body weight 48 hours after induction (Mean ± S.E.) | |
|---|---|---|---|---|
| | | | (g) | (%) |
| Vehicle Control | — | 34.54 ± 0.66 | −0.42 ± 0.16 | −1.21 ± 0.46 |
| 1-43 | 1.5 | 34.74 ± 1.19 | −0.0 ± 0.23 | −0.13 ± 0.71 |
| 2-194 | 1.5 | 35.97 ± 1.15 | 0.10 ± 0.21 | 0.26 ± 0.58 |
| 2-240 | 1.5 | 32.48 ± 0.75 | −0.18 ± 0.04 | −0.56 ± 0.12 |
| DEX | 0.02 | 32.84 ± 0.73 | −1.42 ± 0.20 | −4.30 ± 0.59 |

PHARMACOLOGICAL TEST EXAMPLE 4

Acetic Acid Writhing

This test was carried out referring to the method of Inoue, K., Motonaga, A. & Nishimura, T (*Arzneimittel Forshung/Drug Research*, 41 (1): 235–239 (1991)). More specifically, 7.5 mL/kg of 0.9% acetic acid solution was injected intraperitoneally into an ICR-strain male mouse (5 to 7 weeks old), and the induced writhes (characteristic behaviors of convulsive contracting the abdomen, twisting the body and/or extending the legs) were observed. Number of writhes of each mouse was measured during 10 to 20 min. period after acetic acid administration. The compound of the present invention was homogeneously suspended in 2% Tween 80/saline for injection use, and was injected intraperitoneally 30 min. before the induction by the acetic acid injection. Alternatively, the compound of the present invention was homogeneously suspended in 2% Tween 80/distilled water, and was administered orally two hours before the induction by the acetic acid injection. The analgesic activity of the compounds according to the present invention was evaluated on the basis of the degree of inhibiting the number writhes by the administration of the compounds. As the positive control, indomethacin or aspirin was administrated. The analgesic activity of the compounds according to the present invention measured in this test were exemplified in Table 7.

TABLE 7

| Compound No. | Application route | Dose (mg/kg) | Number of writhes (Mean ± S.E.) |
|---|---|---|---|
| Vehicle Control | i.p. | — | 25.2 ± 2.2 |
| 1-12 | i.p. | 1 | 10.0 ± 1.1 |
| 1-22 | i.p. | 1 | 12.7 ± 4.1 |
| 2-26 | i.p. | 0.3 | 9.8 ± 1.9 |
| 2-135 | i.p. | 1 | 0.8 ± 0.8 |
| 2-189 | i.p. | 1 | 0.8 ± 0.5 |
| Indomethacin | i.p. | 10 | 4.8 ± 0.9 |
| Indomethacin | i.p. | 3 | 13.8 ± 3.0 |
| Aspirin | i.p. | 30 | 9.5 ± 2.0 |

In addition, no remarkable intoxicated symptom was observed on any mouse in the groups, which was injected intravenously in the tails even 100 mg/kg of the compounds according to the present invention.

As it is understood from the results of the foregoing pharmacological tests, it is apparent that the compounds according to the present invention have excellent inhibitory activities on the PLA(2) activity, being less toxic, having strong anti-inflammatory activities and/or anti-allergic activities. Thus, the composites containing the compounds according to the present invention are useful as therapeutic and/or protective drugs of new type, since sick conditions accompanied the activated PLA(2) activity are cured to show excellent effects against such associated diseases, by the administration of the composites.

What is claimed is:

1. A Pharmaceutical composition for an anti-inflammatory drug, and/or an anti-allergic drug, and/or an immune controlling drug, and/or an analgesic drug, the composition having as an active ingredient of a compound represented by a formula (1) and a pharmaceutically acceptable carrier thereof;

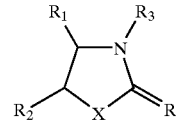

(1)

wherein
  X represents oxygen,
  $R_1$ represents hydrogen, $C_{1-4}$ alkyl or $C_{1-4}$ haloalkyl,
  $R_2$ represents phenyl optionally substituted by $A_1$, naphthyl optionally substituted by $A_1$, quinolyl optionally substituted by $A_1$, R₃ represents hydrogen, $C_{1-4}$ alkyl optionally substituted by A₂, $C_{1-4}$ alkoxy optionally substituted by A₂, $C_{1-4}$ alkylcarbonyl optionally substituted by A₂, $C_{1-4}$ alkoxycarbonyl optionally substituted by A₂, $C_{2-4}$ alkenylcarbonyl optionally substituted by A₂, phenyliminomethyl optionally substituted by A₃, phenyl optionally substituted by A₃, anilino optionally substituted by A₃, or a group represented by the following formulae;

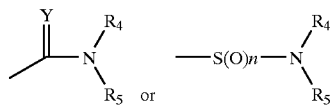

wherein Y represents oxygen or sulfur, R₄ represents hydrogen or $C_{1-4}$ alkyl, R₅ represents $C_{1-6}$ alkyl optionally substituted by A₂, $C_{2-6}$ alkenyl optionally substituted by A₂, $C_{2-6}$ alkynyl optionally substituted by A₂, $C_{1-6}$ alkoxy optionally substituted by A₂, $C_{2-6}$ alkenyloxy optionally substituted by A₂, mono- or di-($C_{1-6}$ alkyl)amino optionally substituted by A₂, $C_{3-7}$ cycloalkyl optionally substituted by A₄, $C_{5-7}$ cycloalkenyl optionally substituted by A₄, phenyl optionally substituted by A₃, benzoyl optionally substituted by A₃, anilino optionally substituted by A₃, $C_{1-6}$ alkoxycarbonyl optionally substituted by A₂, phenylsulfonyl optionally substituted by A₃, $C_{1-6}$ alkoxysulfonyl optionally substituted by A₂, or mono- or di-($C_{1-6}$ alkyl)aminosulfonyl optionally substituted by A₂, and n represents 0, 1 or 2, R represents a group represented by a formula of N—G, wherein G represents hydrogen, nitro, cyano, $C_{1-4}$ alkyl optionally substituted by A₂, $C_{1-4}$ alkoxy, $C_{1-4}$ alkylcarbonyl, phenyl optionally substituted by A₃, benzoyl optionally substituted by A₃, anilino optionally substituted by A₃, a group represented by a formula of NHCOR₆, wherein R₆ represents $C_{1-4}$ alkyl or phenyl optionally substituted by A₃, or a group represented by the following formula;

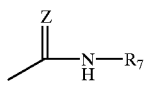

wherein Z represents oxygen or sulfur, R₇ represents $C_{1-4}$ alkyl, $C_{3-7}$ cycloalkyl optionally substituted by A₄, phenyl optionally substituted by A₃, or benzoyl optionally substituted by A₃, A₁ represents halogen, amino, nitro, cyano, $C_{1-12}$ alkyl, $C_{2-6}$ alkenyl, $C_{1-4}$ haloalkyl, $C_{3-7}$ cycloalkyl, phenyl optionally substituted by halogeno, $C_{1-4}$ alkyl or $C_{1-4}$ haloalkyl, $C_{1-4}$ alkoxy, methylenedioxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, benzyl, phenetyl, phenoxy, phenylthio, $C_{1-4}$ alkoxycarbonyl, $C_{1-4}$ haloalkoxycarbonyl, $C_{1-4}$ alkylcarbonyloxy, carbamoyl, or mono- or di-($C_{1-4}$ alkyl)carbamoyl, A₂ represents halogen, $C_{1-4}$ alkoxy, $C_{1-4}$ alkoxy $C_{1-4}$ alkoxy, amino, mono- or di-($C_{1-4}$ alkyl)amino, $C_{1-4}$ alkylcarbonyloxy, $C_{1-4}$ alkoxycarbonyl, halo $C_{1-4}$ alkoxycarbonyl, $C_{1-4}$ alkylcarbamoyl, di-($C_{1-4}$ alkyl) carbonylamino, or phenyl, A₃ represents halogen, hydroxy, oxo, mercapto, nitro, amino, cyano, $C_{1-4}$ alkyl, $C_{1-4}$ haloalkyl, $C_{1-4}$ alkoxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, $C_{1-4}$ alkylcarbonyl, $C_{1-4}$ alkoxycarbonyl, $C_{1-4}$ haloalkoxycarbonyl, carbamoyl, mono- or di-($C_{1-4}$ alkyl)carbamoyl, or $C_{1-4}$ alkoxycarbonyl $C_{1-4}$ alkylthio, and $A_{1-4}$ represents halogen, hydroxy, oxo, $c_{1-4}$ alkyl, halo $C_{1-4}$ alkyl, $C_{1-4}$ alkoxy, $C_{1-4}$ alkylthio, halo $C_{1-4}$ alkoxy, halo $C_{1-4}$ alkylthio, $C_{1-4}$ alkoxy $C_{1-4}$ alkoxy, $C_{1-4}$ alkylsulfonyl, $C_{1-4}$ alkoxycarbonyl, or $C_{1-4}$ haloalkoxycarbonyl.

2. Compounds represented by a formula (1—1);

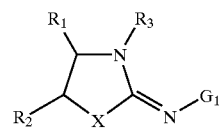

(1-1)

wherein

X represents oxygen,

R₁ represents hydrogen, $C_{1-4}$ alkyl or $C_{1-4}$ haloalkyl,

R₂ represents phenyl optionally substituted by A₁, naphthyl optionally substituted by A₁, quinolyl optionally substituted by A₁, R₃ represents hydrogen, $C_{1-4}$ alkyl optionally substituted by A₂, $C_{1-4}$ alkoxy optionally substituted by $A_{2,\ C1-4}$ alkylcarbonyl optionally substituted by A₂, $A_{1-4}$ alkoxycarbonyl optionally substituted by A₂, $C_{2-4}$ alkenylcarbonyl optionally substituted by A₂, phenyliminomethyl optionally substituted by A₃, phenyl optionally substituted by A₃, anilino optionally substituted by A₃, or a group represented by the following formulae;

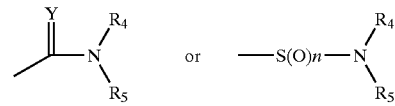

wherein Y represents oxygen or sulfur, R₄ represents hydrogen or $C_{1-4}$ alkyl, R₅ represents $C_{1-6}$ alkyl optionally substituted by A₂, $C_{2-6}$ alkenyl optionally substituted by A₂, $C_{2-6}$ alkynyl optionally substituted by A₂, $C_{1-6}$ alkoxy optionally substituted by A₂, $C_{2-6}$ alkenyloxy optionally substituted by A₂, mono- or di-($C_{1-6}$ alkyl)amino optionally substituted by A₂, $C_{3-7}$ cycloalkyl optionally substituted by A₄, $C_{5-7}$ cycloalkenyl optionally substituted by A₄, phenyl optionally substituted by A₃, benzoyl optionally substituted by A₃, anilino optionally substituted by A₃, $C_{1-6}$ alkoxycarbonyl optionally substituted by A₂, phenylsulfonyl optionally substituted by A₃, $C_{1-6}$ alkoxysulfonyl optionally substituted by A₂, or mono- or di-($C_{1-6}$ alkyl)aminosulfonyl optionally substituted by A₂, and n represents 0, 1 or 2, G₁ represents intro, cyano, $C_{1-4}$ alkylcarbonyl, benzoyl optionally substituted by A₃, NHCOR₆, wherein R₆ represents $C_{1-4}$ alkyl or phenyl optionally substituted by A₃, or a group represented by the following formula;

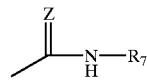

wherein Z represents oxygen or sulfur, R₇ represents $C_{1-4}$ alkyl, $C_{3-7}$ cycloalkyl optionally substituted by A₄, phenyl optionally substituted by A₃, or benzoyl optionally substituted by A₃, A₁ represents halogen, amino, nitro, cyano, $C_{1-12}$ alkyl, $C_{2-6}$ alkenyl, $C_{1-4}$ haloalkyl, $C_{3-7}$ cycloalkyl, phenyl optionally substituted by halogeno, $C_{1-4}$ alkyl or $C_{1-4}$ haloalkyl, $C_{1-4}$ alkoxy, methylenedioxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, benzyl, phenetyl, phenoxy, phenylthio, $C_{1-4}$ alkoxycarbonyl, $C_{1-4}$ haloalkoxycarbonyl, $C_{1-4}$ alkylcarbonyloxy, carbamoyl, or mono- or di-($C_{1-4}$ alkyl)carbamoyl, $A_2$ represents halogen, $C_{1-4}$ alkoxy, $C_{1-4}$ alkoxy $C_{1-4}$ alkoxy, amino, mono- or di-($C_{1-4}$ alkyl)amino, $C_{1-4}$ alkylcarbonyloxy, $C_{1-4}$ alkoxycarbonyl, halo $C_{1-4}$ alkoxycarbonyl, $C_{1-4}$ alkylcarbamoyl, di-($C_{1-4}$ alkyl) carbonylamino, or phenyl, $A_3$ represents halogen, hydroxy, oxo, mercapto, nitro, amino, cyano, $C_{1-4}$ alkyl, $C_{1-4}$ haloalkyl, $C_{1-4}$ alkoxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, $C_{1-4}$ alkylcarbonyl, $C_{1-4}$ alkoxycarbonyl, $C_{1-4}$ haloalkoxycarbonyl, carbamoyl, mono- or di-($C_{1-4}$ alkyl)carbamoyl, or $C_{1-4}$ alkoxycarbonyl $C_{1-4}$ alkylthio, and $A_4$ represents halogen, hydroxy, oxo, $C_{1-4}$ alkyl, halo $C_{1-4}$ alkyl $C_{1-4}$ alkoxy, $C_{1-4}$ alkylthio, halo $C_{1-4}$ alkoxy, halo $C_{1-4}$ alkylthio, $C_{1-4}$ alkoxy $C_{1-4}$ alkoxy, $C_{1-4}$ alkylsulfonyl, $C_{1-4}$ alkoxycarbonyl, or $C_{1-4}$ haloalkoxycarbonyl.

3. A method to treat inflammatory diseases or disorders allergic diseases or auto-immune diseases by administering an effective amount of a pharmaceutical composition of a of compound of formula (1) and the pharmaceutically acceptable carrier thereof, to a mammal,

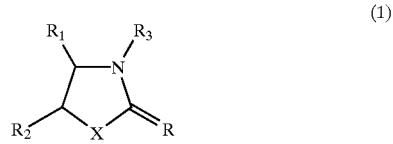

(1)

wherein
X represents oxygen,
$R_1$ represents hydrogen, $C_{1-4}$ alkyl or $C_{1-4}$ haloalkyl,
$R_2$ represents phenyl optionally substituted by $A_1$, naphthyl optionally substituted by $A_1$, quinolyl optionally substituted by $A_1$,
$R_3$ represents hydrogen, $C_{1-4}$ alkyl optionally substituted by $A_2$, $A_{1-4}$ alkoxy optionally substituted by $A_2$, $C_{1-4}$ alkylcarbonyl optionally substituted by $A_2$, $C_{1-4}$ alkoxycarbonyl optionally substituted by $A_2$, $C_{2-4}$ alkenylcarbonyl optionally substituted by $A_2$, phenyliminomethyl optionally substituted by $A_3$, phenyl optionally substituted by $A_3$, anilino optionally substituted by $A_3$, or a group represented by the following formulae;

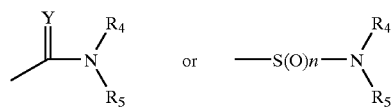

wherein Y represents oxygen or sulfur, $R_4$ represents hydrogen or $C_{1-4}$ alkyl, $R_5$ represents $C_{1-6}$ alkyl optionally substituted by $A_2$, $A_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, benzoyl optionally substituted by $A_3$, anilino optionally substituted by $A_3$, $C_{1-6}$ alkoxycarbonyl optionally substituted by $A_2$, phenylsulfonyl optionally substituted by $A_3$, $C_{1-6}$ alkoxysulfonyl optionally substituted by $A_2$, or mono- or di-($C_{1-6}$ alkyl)aminosulfonyl optionally substituted by $A_2$, and n represents 0, 1 or 2, R represents a group represented by a formula of N—G, wherein G represents hydrogen, nitro, cyano, $C_{1-4}$ alkyl optionally substituted by $A_{1-4}$ alkoxy, $C_{1-4}$ alkylcarbonyl, phenyl optionally substituted by $A_3$, benzoyl optionally substituted by $A_3$, anilino optionally substituted by $A_3$, a group represented by a formula of $NHCOR_6$, wherein $R_6$ represents $C_{1-4}$ alkyl or phenyl optionally substituted by $A_3$, or a group represented by the following formula;

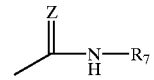

wherein Z represents oxygen or sulfur, $R_7$ represents $C_{1-4}$ alkyl, $C_{3-7}$ cycloalkyl optionally substituted by $A_4$, phenyl optionally substituted by $A_3$, or benzoyl optionally substituted by $A_3$;

$A_1$ represents halogen, amino, nitro, cyano, $C_{1-12}$ alkyl, $C_{2-6}$ alkenyl, $C_{1-4}$ haloalkyl, $C_{3-7}$ cycloalkyl, phenyl optionally substituted by halogeno, $C_{1-4}$ alkyl or $C_{1-4}$ haloalkyl, $C_{1-4}$ alkoxy, methylenedioxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, benzyl, phenetyl, phenoxy, phenylthio, $C_{1-4}$ alkoxycarbonyl, $C_{1-4}$ haloalkoxycarbonyl, $C_{1-4}$ alkylcarbonyloxy, carbamoyl, or mono- or di-($C_{1-4}$ alkyl)carbamoyl, $A_2$ represents halogen, $C_{1-4}$ alkoxy, $C_{1-4}$ alkoxy $C_{1-4}$ alkoxy, amino, mono- or di-($C_{1-4}$ alkyl)amino, $C_{1-4}$ alkylcarbonyloxy, $C_{1-4}$ alkoxycarbonyl, halo $C_{1-4}$ alkoxycarbonyl, $C_{1-4}$ alkylcarbamoyl, di-($C_{1-4}$ alkyl) carbonylamino, or phenyl, $A_3$ represents halogen, hydroxy, oxo, mercapto, nitro, amino, cyano, $C_{1-4}$ alkyl, $C_{1-4}$ haloalkyl, $C_{1-4}$ alkoxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, $C_{1-4}$ alkylcarbonyl, $C_{1-4}$ alkoxycarbonyl, $C_{1-4}$ haloalkoxycarbonyl, carbamoyl, mono- or di-($C_{1-4}$ alkyl)carbamoyl, or $C_{1-4}$ alkoxycarbonyl $C_{1-4}$ alkylthio, and $A_4$ represents halogen, hydroxy, oxo, $C_{1-4}$ alkyl, halo $C_{1-4}$ alkyl, $C_{1-4}$ alkoxy, $C_{1-4}$ alkylthio, halo $C_{1-4}$ alkoxy, halo $C_{1-4}$ alkylthio, $C_{1-4}$ alkoxy $C_{1-4}$ alkoxy, $C_{1-4}$ alkylsulfonyl, $C_{1-4}$ alkoxycarbonyl, or $C_{1-4}$ haloalkoxycarbonyl.

4. The method according to claim 3, wherein the inflammatory diseases or the disorders are any of anaphylaxis, allergic inflammation, asthma, rhinitis, bronchitis, pneumonia, and adult respiratory distress syndrome, inflammatory intestine disorder, Crohn's disease, ulcerative colitis, ischemia/reperfusion injuries, vasculitis, arteriosclerosis, hepatitis, nephritis, nerve degenerative diseases, arthritis, dermatitis, solar keratosis, psoriasis, septic shock and fever.

5. The method according to claim 3, wherein the progress of the sick condition is due to inflammatory disease or disorder that is accompanied with the enhanced phospholipase A(2) activity.

6. The method according to claim 3, wherein the inflammatory disease or disorder is mediated by pro-inflammatory lipid mediators, such as arachidonic acid and the metabolites thereof, and/or lysophosphatidylcholine, and/or the platelet activating factor (PAF).

7. The method according to claim 6, wherein the pro-inflammatory lipid mediators are suppressed by the inhibitor of the phospholipase A(2) activity.

8. A method for treating a patient in order to reduce inflammatory and/or allergic conditions and/or sick conditions associated with auto-immune diseases and disorders, the method comprising administering to said patient a medicinal composition manufactured from a compound of the formula (1)

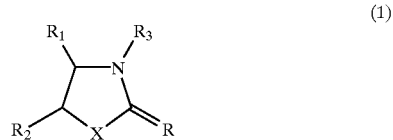

(1)

wherein

X represents oxygen, $R_1$ represents hydrogen, $C_{1-4}$ alkyl or $C_{1-4}$ haloalkyl, $R_2$ represents phenyl optionally substituted by $A_1$, naphthyl optionally substituted by $A_1$, quinolyl optionally substituted by $A_1$, $R_3$ represents hydrogen, $C_{1-4}$ alkyl optionally substituted by $A_2$, $C_{1-4}$ alkoxy optionally substituted by $A_2$, $C_{1-4}$ alkylcarbonyl optionally substituted by $A_2$, $C_{1-4}$ alkoxycarbonyl optionally substituted by $A_2$, $A_{2-4}$ alkenylcarbonyl optionally substituted by $A_2$, phenyliminomethyl optionally substituted by $A_3$, phenyl optionally substituted by $A_3$, anilino optionally substituted by $A_3$, or a group represented by the following formulae;

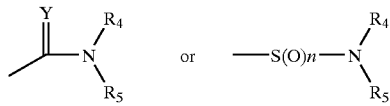

wherein Y represents oxygen or sulfur, $R_4$ represents hydrogen or $C_{1-4}$ alkyl, $R_5$ represents $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$ phenyl optionally substituted by $A_3$, benzoyl optionally substituted by $A_3$, anilino optionally substituted by $A_3$, $C_{1-6}$ alkoxycarbonyl optionally substituted by $A_2$, phenylsulfonyl optionally substituted by $A_3$, $C_{1-6}$ alkoxysulfonyl optionally substituted by $A_2$, or mono- or di-($C_{1-6}$ alkyl)aminosulfonyl optionally substituted by $A_2$, and n represents 0, 1 or 2, R represents a group represented by a formula of N—G, wherein G represents hydrogen, nitro, cyano, $C_{1-4}$ alkyl optionally substituted by $A_2$, $C_{1-4}$ alkoxy, $C_{1-4}$ alkylcarbonyl, phenyl optionally substituted by $A_3$, benzoyl optionally substituted by $A_3$, anilino optionally substituted by $A_3$, a group represented by a formula of $NHCOR_6$, wherein $R_6$ represents $C_{1-4}$ alkyl or phenyl optionally substituted by $A_3$, or a group represented by the following formula;

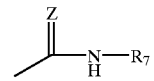

wherein Z represents oxygen or sulfur, $R_7$ represents $C_{1-4}$ alkyl, $C_{3-7}$ cycloalkyl optionally substituted by $A_4$, phenyl optionally substituted by $A_3$, or benzoyl optionally substituted by $A_3$, $A_1$ represents halogen, amino, nitro, cyano, $C_{1-12}$ alkyl, $C_{2-6}$ alkenyl, $C_{1-4}$ haloalkyl, $C_{3-7}$ cycloalkyl, phenyl optionally substituted by halogeno, $C_{1-4}$ alkyl or $C_{1-4}$ haloalkyl, $C_{1-4}$ alkoxy, methylenedioxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, benzyl, phenetyl, phenoxy, phenylthio, $C_{1-4}$ alkoxycarbonyl, $C_{1-4}$ haloalkoxycarbonyl, $C_{1-4}$ alkylcarbonyloxy, carbamoyl, or mono- or di-($C_{1-4}$ alkyl)carbamoyl, $A_2$ represents halogen, $C_{1-4}$ alkoxy, $C_{1-4}$ alkoxy $C_{1-4}$ alkoxy, amino, mono- or di-($C_{1-4}$ alkyl)amino, $C_{1-4}$ alkylcarbonyloxy, $C_{1-4}$ alkoxycarbonyl, halo $C_{1-4}$ alkoxycarbonyl, $C_{1-4}$ alkylcarbamoyl, di-($C_{1-4}$ alkyl)carbonylamino, or phenyl, $A_3$ represents halogen, hydroxy, oxo, mercapto, nitro, amino, cyano, $C_{1-4}$ alkyl, $C_{1-4}$ haloalkyl, $C_{1-4}$ alkoxy, $C_{1-4}$ alkylthio, $C_{1-4}$ alkylsulfenyl, $C_{1-4}$ alkylsulfonyl, mono- or di-($C_{1-4}$ alkyl)amino, $C_{1-4}$ haloalkoxy, $C_{1-4}$ alkylcarbonyl, $C_{1-4}$ alkoxycarbonyl, $C_{1-4}$ haloalkoxycarbonyl, carbamoyl, mono- or di-($C_{1-4}$ alkyl)carbamoyl, or $C_{1-4}$ alkoxycarbonyl $C_{1-4}$ alkylthio, and $A_4$ represents halogen, hydroxy, oxo, $C_{1-4}$ alkyl, halo $C_{1-4}$ alkyl, $C_{1-4}$ alkoxy, $C_{1-4}$ alkylthio, halo $C_{1-4}$ alkoxy, halo $C_{1-4}$ alkylthio, $C_{1-4}$ alkoxy $C_{1-4}$ alkoxy, $C_{1-4}$ alkylsulfonyl, $C_{1-4}$ alkoxycarbonyl, or $C_{1-4}$ haloalkoxycarbonyl.

\* \* \* \* \*

UNITED STATES PATENT AND TRADEMARK OFFICE
CERTIFICATE OF CORRECTION

PATENT NO. : 6,762,200 B2
DATED : July 13, 2004
INVENTOR(S) : Masae Takagi et al.

It is certified that error appears in the above-identified patent and that said Letters Patent is hereby corrected as shown below:

Column 3,
Line 49, replace "—(CH2)$_4$— or" with -- —(CH$_2$)$_4$— --

Column 16,
Line 25, replace "1.8g of threo2-amino-1-(4-chlorophenyl)propanol" with
-- 1.8g of threo-2-amino-1-(4-chlorophenyl)propanol --

Column 17-18,
Table 1, replace "existing formula in heading" with
--  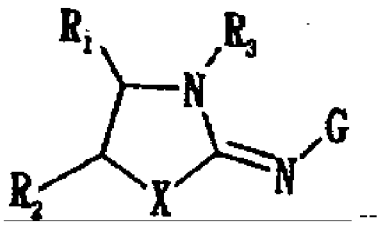  --

Column 19-20,
Table 1-continuted, replace "existing formula in heading" with
--  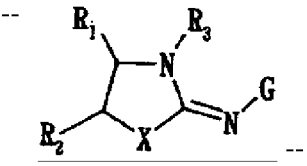  --

Signed and Sealed this

Fifteenth Day of February, 2005

JON W. DUDAS
*Director of the United States Patent and Trademark Office*